(12) United States Patent
Kozlov et al.

(10) Patent No.: US 7,229,769 B2
(45) Date of Patent: Jun. 12, 2007

(54) COMPOSITIONS AND METHODS FOR DETECTING PROTEASE ACTIVITY

(75) Inventors: Igor Kozlov, La Jolla, CA (US); Peter Melnyk, La Mesa, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 11/090,904

(22) Filed: Mar. 25, 2005

(65) Prior Publication Data

US 2006/0216721 A1  Sep. 28, 2006

(51) Int. Cl.
*A61K 36/06* (2006.01)
(52) U.S. Cl. .......................................... 435/6
(58) Field of Classification Search ................ 435/6
See application file for complete search history.

(56) References Cited

U.S. PATENT DOCUMENTS

| | | | |
|---|---|---|---|
| 4,569,794 A | 2/1986 | Smith et al. | |
| 4,877,830 A | 10/1989 | Dobeli et al. | |
| 5,047,513 A | 9/1991 | Dobeli et al. | |
| 5,284,933 A | 2/1994 | Dobeli et al. | |
| 5,310,663 A | 5/1994 | Dobeli et al. | |
| 6,238,869 B1* | 5/2001 | Kris et al. | 435/6 |
| 6,243,980 B1 | 6/2001 | Bronstein et al. | |
| 6,395,474 B1 | 5/2002 | Buchardt et al. | |
| 2001/0046680 A1* | 11/2001 | Yu | 435/6 |

OTHER PUBLICATIONS

Kozlov et al. Biopolymers 73, 621-630 in print Apr. 5, 2004, on web Mar. 8, 2004. Efficient strategies for the conjugation of oligonucleotides to antibodies enabling highly sensitive protein detection.*
Manzini et al. Biophysical Chem 10(3-4), 397-407 Nov. 1979. On the comtemporaneous, reversible interaction of different ligands with serum albumins in dilute aqueous solutions—Fluorescein and phenylbutazone.*
Winssinger et al. Angew. Chem Int. Ed.40(17), 3152-3155. From split-pool libraries to spatially addressable microarrays and its application to functional proteomic profiling, 2001.*
Stedman's Medical Dictionary, 24th Edition, Williams and Wilkins, Baltimore, 1982, p. 1154, Column 1, Lines 20-21.*
Burbulis, I. et al., Using protein-DNA chimeras to detect and count small numbers of molecules, Nature Methods, 2(1):31-37 (2005).
Craig, D. et al., General Protease Assay Method Coupling Solid-Phase Substrate Extraction and Capillary Electrophoresis, Analytical Chemistry, 70:3824-3827 (1998).
Hochuli, E. et al., New Metal Chelate Adsorbent Selective for Proteins and Peptides Containing Neighbouring Histidine Residues, Journal of Chromatography, 411:177-184 (1987).
Hochuli, E. et al., Genetic Approach to Fascilitate Purification of Recombinant Proteins with a Novel Metal Chelate Adsorbent, Bio/Technology, 6:1321-1325 (1988).
Manetta, J. et al., Design and Implementation of a Particle Concentration Fluorescence Method for the Detection of HIV-1 Protease Inhibitors, Anal. Biochem., 202:10-15 (1992).
Terpe, K., Overview of tag protein fusions: from molecular and biochemical fundamentals to commercial systems, Appl. Microbiol. Biotechnol., 60:523-533 (2003).
Tung, C., Preparation and Applications of Peptide-Oligonucleotide Conjugates, Bioconjugate Chemistry, 11(5):605-618 (2000).
Zubin, E. M. et al., Modern methods for the synthesis of peptide-oligonucleotide conjugates, Russian Chemical Reviews, 71(3):239-264 (2002).

* cited by examiner

*Primary Examiner*—Jon Weber
*Assistant Examiner*—Kailash C. Srivastava
(74) *Attorney, Agent, or Firm*—John T. Murphy

(57) ABSTRACT

The invention provides a method of determining activity of a protease. The method can include the steps of (a) providing a protease substrate including a protein moiety attached to a nucleic acid moiety and a ligand moiety; (b) contacting the protease substrate with a protease under conditions wherein the protease catalyzes cleavage of the protein moiety, thereby producing a proteolytic product wherein the nucleic acid moiety is separated from at least a portion of the protein moiety and the ligand moiety; (c) contacting the proteolytic product with a receptor under conditions wherein the ligand moiety binds to the receptor to form a complex; (d) separating the complex from the nucleic acid moiety, thereby forming a separation product including the nucleic acid moiety; (e) contacting the separation product with a probe nucleic acid under conditions wherein the nucleic acid moiety hybridizes to a complementary sequence of the probe; and (f) detecting hybridization of the separation product to the probe, thereby determining activity of the protease.

30 Claims, 12 Drawing Sheets

COMPOSITIONS AND METHODS FOR DETECTING PROTEASE ACTIVITY

This invention was made with government support under grant number AI056869 awarded by the National Institute of Health. The United States Government has certain rights in this invention.

BACKGROUND OF THE INVENTION

This invention relates generally to proteomics, and more specifically to detection of protease activity in formats amenable to multiplex analysis.

Proteases are a class of enzymes with important roles in the regulation of cellular activity. Proteases act by cleaving proteins into smaller versions. This results in activation or inactivation of the proteins which in turn influences the role of the proteins in diverse physiological processes. Examples of physiological processes that are directly affected by proteases include blood coagulation, inflammation, programmed cell death, reproduction, fibrinolysis, and immune response. Numerous disease states are caused by, or can be characterized by, the alterations in the activity of specific proteases. The importance and complexity of the roles played by proteases in human health is evident in the fact that there are at least 575 known and putative proteases in humans, and it is estimated that up to 1,200 human genes encode proteases. The ability to detect and evaluate these proteases in research or clinically is significant to the investigation, treatment, and management of disease states.

In addition, there are many pathogenic microorganisms that depend upon specific protease activity for their infectivity. As an example, many viruses depend on protease cleavage of inactive precursors, called pro-proteins, to form active products that mediate infection. Inhibiting such selective cleavage can inhibit the viability of the virus. Again, the ability to evaluate these proteases in a research or clinical setting would benefit investigation, treatment and management of many pathogenic diseases.

Several blockbuster drugs that have been introduced to the market are protease inhibitors. For example, protease inhibitor drugs have been developed to inhibit viral proteases required for replication of HIV and in many cases have been the most effective treatments for HIV/AIDS. Other protease inhibitor drugs block the human protease, thrombin, which is involved in blood clotting and are among the most effective treatments for stroke and coronary infarction. Protease inhibitor drugs are also used to treat high blood pressure. Overall, it has been estimated that 5-10% of all pharmaceutical targets are proteases. In this regard, other protease inhibitors are being developed to treat parasitic, fungal, and viral infections; inflammatory, immunological, and respiratory conditions; cardiovascular and neurodegenerative disorders including Alzheimer's disease; and cancers.

Proteases are also important in food processing. Some well known examples are the production of cheese which has traditionally relied upon proteases isolated from the stomach of unweaned calves and meat tenderization which traditionally utilized papain from the leaves and unripe fruit of Carica papaya. Proteases are also used in the baking industry. For example, pastry dough may be prepared more quickly if its gluten is partially hydrolyzed using a heat-labile protease that is inactivated early in the subsequent baking. Although several traditional methods are still practiced in food processing, there is a need for new proteases that provide more efficient food production or new varieties and flavors. For example, the amount and types of proteases used during cheese ripening has substantial effects on flavor and quality. As such differences in proteases used for cheese ripening is largely responsible for the distinct varieties of cheeses available.

In a further example, proteolysis of inexpensive materials such as soya protein can increase the range and value of their usage in producing new foods. In this regard, partial hydrolysis of soya protein can greatly increase its 'whipping expansion' whereas further hydrolysis can improve its emulsifying capacity. Proteases can also be used to recover protein from parts of animals that would otherwise go to waste after butchering. For example, residual meat on manually butchered bones can be removed by proteases and the resulting meat slurry used to provide canned meats and soups.

Traditionally, however proteases have not always been easy to evaluate and identify. Although specific assays have been developed to measure activity of individual proteases, their utility for evaluating proteases in more complex biological mixtures has been limited. Furthermore, the ability to identify new substrates or inhibitors for proteases is often difficult using assays for individual proteases. The result is inefficient identification of useful proteases and or inhibitors.

Thus, there exists a need for assays that allow the rapid and efficient analysis of protease activity in complex biological mixtures. There is also a need for assays to identify previously unknown protease substrates or inhibitors. The present invention satisfies these needs and provides other advantages as well.

BRIEF SUMMARY OF THE INVENTION

The invention provides a method of determining activity of a protease. The method can include the step of (a) providing a protease substrate including a protein moiety attached to a nucleic acid moiety; (b) contacting the protease substrate with a protease under conditions wherein the protease catalyzes cleavage of the protein moiety, thereby producing a proteolytic product wherein the nucleic acid moiety is separated from the protein moiety; (c) contacting the proteolytic product with a nucleic acid probe under conditions wherein the nucleic acid moiety hybridizes to a complementary sequence of the probe; and (d) detecting hybridization of the proteolytic product to the probe, thereby determining activity of the protease.

The invention also provides a method of determining activity of at least one protease. The method can include the steps of (a) providing a plurality of different protease substrates each including a protein moiety attached to a nucleic acid moiety, wherein the sequence of each nucleic acid moiety is unique to the sequence of a different protein moiety; (b) contacting the protease substrates with at least one protease under conditions wherein the at least one protease catalyzes cleavage of the protein moieties, thereby producing proteolytic products each wherein the nucleic acid moiety is separated from the protein moiety; (c) contacting the proteolytic products each with nucleic acid probes under conditions wherein the nucleic acid moiety hybridizes to a complementary sequences of the probe; and (d) detecting hybridization of the proteolytic products to the probes, thereby determining activity of the at least one protease.

The invention further provides method of determining activity of a protease. The method can include the steps of (a) providing a protease substrate including a protein moiety attached to a nucleic acid moiety and a ligand moiety; (b) contacting the protease substrate with a protease under conditions wherein the protease catalyzes cleavage of the protein moiety, thereby producing a proteolytic product wherein the nucleic acid moiety is separated from at least a portion of the protein moiety and the ligand moiety; (c) contacting the proteolytic product with a receptor under conditions wherein the ligand moiety binds to the receptor to form a complex; (d) separating the complex from the nucleic acid moiety, thereby forming a separation product including the nucleic acid moiety; (e) contacting the separation product with a probe nucleic acid under conditions wherein the nucleic acid moiety hybridizes to a complementary sequence of the probe; and (f) detecting hybridization of the separation product to the probe, thereby determining activity of the protease.

Also provided is a method of determining activity of at least one protease, including the steps of (a) providing a plurality of protease substrates each including a protein moiety attached to a nucleic acid moiety and a ligand moiety, wherein the sequence of each nucleic acid moiety is unique to the sequence of a different protein moiety; (b) contacting the protease substrates with at least one protease under conditions wherein the at least one protease catalyzes cleavage of the protein moieties, thereby producing proteolytic products wherein the nucleic acid moieties are separated from at least a portion of the protein moieties and the ligand moieties; (c) contacting the proteolytic products with at least one receptor under conditions wherein the ligand moieties bind to the at least one receptor to form complexes; (d) separating the complexes from the nucleic acid moieties, thereby forming separation products including the nucleic acid moieties; (e) contacting the separation products with nucleic acid probes under conditions wherein the nucleic acid moieties hybridize to complementary sequences of the probes; and (f) detecting hybridization of the separation products to the probes, thereby determining activity of the at least one protease.

DETAILED DESCRIPTION OF THE INVENTION

Figure 1:
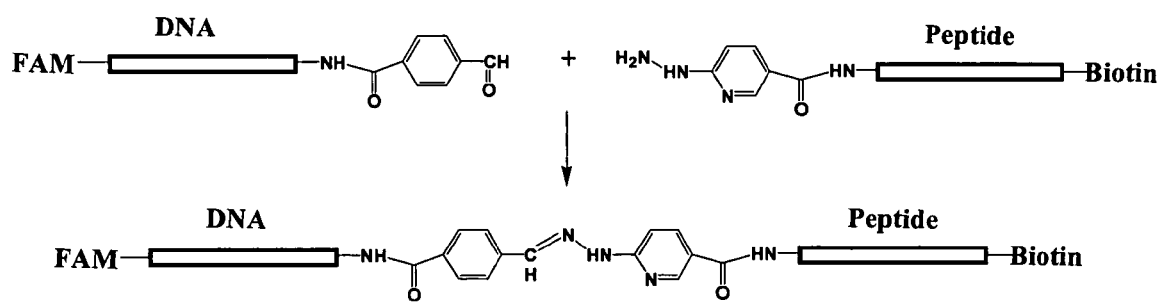
FIG. 1 shows a method for attaching a DNA moiety to a protein moiety.

This invention provides compositions and methods for evaluating protease activity. The methods are well suited for multiplex analysis of pluralities of proteases, protease substrates or protease inhibitors or combinations thereof. However, if desired the methods or compositions can be used in a singleplex format (i.e. using a single species of protease and a single species of protease substrate). An advantage of the invention is that the use of a multiplex format allows for increased efficiency and reduced reagent consumption for determining protease activity. Moreover, the use of a multiplex format can allow convenient evaluation of the effects of complex mixtures on protease activity and can, therefore, more appropriately simulate the complex mixture experienced by proteases in their natural milieu compared to the use of most currently available protease assays.

Definitions

As used herein, the term "protease" is intended to mean an agent that catalyzes the cleavage of peptide bonds in a protein. A protease can have sequence specificity, splitting a peptide bond of a protein based on the presence of a particular amino acid sequence in the protein. However, non-sequence specific proteases are also useful. A protease can be characterized according to the location in a protein where it cleaves, an endoprotease cleaving a protein between internal amino acids of an amino acid chain and an exoprotease cleaving a protein to remove an amino acid from the end of an amino acid chain. A protease can be characterized according to mechanism of action, being identified, for example, as a serine protease, cysteine (thiol) protease, aspartic (acid) protease, metalloprotease or mixed protease depending on the principal amino acid participating in catalysis. A protease can also be classified based on the action pattern, examples of which include an aminopeptidase which cleaves an amino acid from the amino end of a protein, carboxypeptidase which cleaves an amino acid from the carboxyl end of a protein, dipeptidyl peptidase which cleaves two amino acids from an end of a protein, dipeptidase which splits a dipeptide and tripeptidase which cleaves an amino acid from a tripeptide. Typically, a protease is a protein enzyme. However, non-protein agents capable of catalyzing the cleavage of peptide bonds in a protein, especially in a sequence specific manner are also useful in the invention.

As used herein, the term "activity," when used in reference to a protease, is intended to mean binding of the protease to a protease substrate or hydrolysis of the protease substrate or both. The activity can be indicated, for example, as binding specificity, catalytic activity or a combination thereof. The activity of a protease can be identified qualitatively or quantitatively in accordance with the compositions and methods disclosed herein. Exemplary qualitative measures of protease activity include, without limitation, identification of a substrate cleaved in the presence of the protease, identification of a change in substrate cleavage due to presence of another agent such as an inhibitor or activator, identification of an amino acid sequence that is recognized by the protease, identification of the composition of a substrate recognized by the protease or identification of the composition of a proteolytic product produced by the protease. Activity can be quantitatively expressed as units per milligram of enzyme (specific activity) or as molecules of substrate transformed per minute per molecule of enzyme (molecular activity). The conventional unit of enzyme activity is the International Unit (IU), equal to one micromole of substrate transformed per minute. A proposed coherent Système Internationale (SI) unit is the katal (kat), equal to one mole of substrate transformed per second.

As used herein the term, "protease substrate" is intended to mean a molecule that can be cleaved by a protease. A protease substrate is typically a protein or protein moiety having an amino acid sequence that is recognized by a protease. A protease can recognize the amino acid sequence of a protease substrate due to the specific sequence of side chains or due to properties generic to proteins. A protease substrate can also be a protein mimetic or non-protein molecule that is capable of being cleaved or otherwise covalently modified by a protease.

As used herein, the term "proteolytic product" is intended to mean at least one molecule that has been cleaved by a protease. A protease can produce one, two or more proteolytic products. For example, two molecules can be produced when a molecule is cleaved by a protease and the portions on either side of the protease cleavage site are not otherwise tethered to each other. A single molecule can result in cases where portions on either side of a cleaved site are tethered to each other, for example, via a disulfide linkage or non-covalent interaction. Several products can result when a protein or protein moiety is cleaved at several locations and the portions on either side of the protease cleavage sites are not otherwise tethered to each other.

As used herein, the term "level," when used in reference to a reaction product, is intended to mean an amount of the reaction product or of a characteristic of the reaction product. An amount of a reaction product or characteristic of the reaction product can be expressed in absolute terms or relative terms. Exemplary absolute amounts include, but are not limited to, number of molecules, mass, concentration, catalytic activity, generated signal such as an optical signal, or other amounts known in the art and measurable by known methods. Exemplary relative amounts include, without limitation, a ratio of the foregoing amounts for two different reaction products or two different populations of reaction products. The characteristic of a reaction product can be detected by methods described herein or otherwise known in the art such as optical spectroscopy, mass spectroscopy, detection of magnetic or electronic properties or calorimetry.

As used herein, the term "protein" is intended to mean a chain of amino acids connected by peptide bonds. The term is intended to include chains having any possible number of amino acids, unless explicitly indicated otherwise. Accordingly a protein can include a single linear chain having at least about 2, 3, 4, 5, 6, 7, 8, 9, 10, 15, 20, 25, 50, 100, 1000, 10,000, 100,000 or more amino acids. If desired, a protein useful in the invention can have a maximum length including, for example, at most about 100,000, 10,000, 1000, 100, 10, 5 or fewer in a linear chain. A protein can include one or more of the 20 amino acids used by a human cell to translate RNA into protein. Furthermore, a protein can include other amino acids such as non-naturally occurring amino acids.

A protein when included as part of a larger molecule or substrate is referred to herein as a "protein moiety." For example, a protein moiety can be covalently attached to another protein moiety or to a moiety having other compositions such as a nucleic acid, polysaccharide, phosphate, isoprenyl group or enzyme cofactor. A protein moiety can be attached to another protein moiety via a peptide bond to form a linear chain. Alternatively or additionally, a protein moiety can be attached to another protein moiety to form a branched chain, for example, via the thioether linkage of cystine or via an isopeptide bond such as that formed between the alpha carboxy of ubiquitin and the epsilon amino group in the side chain of a lysine residue. A protein moiety can be non-covalently attached with another moiety or molecule such as a second protein or a nucleic acid. A species of proteins or protein moieties is understood to be a group that all include the same sequence of amino acids As used herein, the term "nucleic acid" is intended to mean polymer molecule composed of subunits having purine or pyrimidine bases. A nucleic acid when included as part of a larger molecule is referred to herein as a "nucleic acid moiety." A nucleic acid useful in the present invention will generally contain phosphodiester bonds, and can include, for example, DNA or RNA. If desired to suit a particular application, DNA or RNA analogs having alternate backbones can be used, including, for example, phosphoramide (Beaucage et al., *Tetrahedron* 49(10): 1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphosphoroamidite linkages (see Eckstein, *Oligonucleotides and Analogues: A Practical Approach*, Oxford University Press), or peptide nucleic acid linkages (see Egholm, *J. Am. Chem. Soc.* 114:1895 (1992); Meier et al., *Chem. Int. Ed. Engl.* 31:1008 (1992); Nielsen, *Nature*, 365:566 (1993); Carlsson et al., *Nature* 380:207 (1996), all of which are incorporated by reference). Other polynucleotide analogs include those with positive backbones (Denpcy et al., *Proc. Natl. Acad. Sci. USA* 92:6097

(1995); non-ionic backbones (U.S. Pat. Nos. 5,386,023, 5,637,684, 5,602,240, 5,216,141 and 4,469,863; Kiedrowshi et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, *ASC Symposium Series* 580, "Carbohydrate Modifications in Antisense Research", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non-ribose backbones, including those described in U.S. Pat. Nos. 5,235,033 and 5,034,506, and Chapters 6 and 7, *ASC Symposium Series* 580, "Carbohydrate Modifications in Antisense Research", Ed. Y. S. Sanghui and P. Dan Cook. Nucleic acids containing one or more carbocyclic sugars can also be used in the invention (see Jenkins et al., *Chem. Soc. Rev.* (1995) pp 169-176). Several other nucleic acid analogs are described in Rawls, *C & E News* Jun. 2, 1997 page 35.

A nucleic acid or nucleic acid moiety can be single stranded, double stranded or contain portions of both double stranded and single stranded sequence. A polynucleotide can be DNA, such as genomic DNA (gDNA) or copy DNA (cDNA); RNA such as messenger RNA (mRNA), transfer RNA (tRNA) or ribosomal RNA (rRNA); or a hybrid containing any combination of deoxyribo- and ribo-nucleotides or any combination of bases, including uracil, adenine, thymine, cytosine, guanine, inosine, xanthanine, hypoxanthanine, isocytosine, isoguanine, or the like. A "species" of nucleic acids or nucleic acid moieties is understood to be a group that all include the same nucleic acid sequence.

As used herein, the term "label moiety" is intended to mean one or more atoms that can be specifically detected to indicate the presence of a substance to which the one or more atom is attached. A label moiety can be a primary label that is directly detectable or secondary label that can be indirectly detected, for example, via interaction with a primary label. Exemplary primary labels include, without limitation, an isotopic label such as a naturally non-abundant heavy isotope or radioactive isotope, examples of which include $^{14}C$, $^{123}I$, $^{124}I$, $^{125}I$, $^{131}I$, $^{32}P$, $^{35}S$ or $^{3}H$; optically detectable moieties such as a chromophore, luminophore, fluorophore, quantum dot or nanoparticle; electromagnetic spin label; calorimetric agent; magnetic substance; electron-rich material such as a metal; electrochemiluminescent label such as $Ru(bpy)_3^{2+}$; moiety that can be detected based on a nuclear magnetic, paramagnetic, electrical, charge to mass, or thermal characteristic; or light scattering or plasmon resonant materials such as gold or silver particles. Fluorophores that are useful in the invention include, for example, fluorescent lanthanide complexes, including those of Europium and Terbium, fluorescein, fluorescein isothiocyanate, carboxyfluorescein (FAM), dichlorotriazinylamine fluorescein, rhodamine, tetramethylrhodamine, umbelliferone, eosin, erythrosin, coumarin, methyl-coumarins, pyrene, Malacite green, Cy3, Cy5, stilbene, Lucifer Yellow, Cascade Blue™, Texas Red, alexa dyes, dansyl chloride, phycoerythin, green fluorescent protein and its wavelength shifted variants, bodipy, and others known in the art such as those described in Haugland, *Molecular Probes Handbook*, (Eugene, Oreg.) 6th Edition; The Synthegen catalog (Houston, Tex.), Lakowicz, *Principles of Fluorescence Spectroscopy*, 2nd Ed., Plenum Press New York (1999), or WO 98/59066.

Exemplary secondary labels that can be used in the invention include, without limitation, a binding moiety such as a receptor, ligand or other member of a pair of molecules having binding specificity for each other. Exemplary binding moieties having specificity for each other include, without limitation, streptavidin & biotin, avidin & biotin or an antigen & antibody such as rabbit IgG & anti-rabbit IgG. Specific affinity between two binding partners is understood to mean preferential binding of one partner to another compared to binding of the partner to other components or contaminants in the system. Binding partners that are specifically bound typically remain bound under the detection or separation conditions described herein, including wash steps to remove non-specific binding. Depending upon the particular binding conditions used, the dissociation constants of the pair can be, for example, less than about $10^{-4}$, $10^{-5}$, $10^{-6}$, $10^{-7}$, $10^{-8}$, $10^{-9}$, $10^{-10}$, $10^{-11}$, or $10^{-12}$ $M^{-1}$. Secondary labels also include enzymes or their substrates, wherein the combination produces a detectable product, examples of which include horseradish peroxidase, alkaline phosphatase, β-galactosidase, or acetylcholinesterase which produce colorimetric products using color reagents that are commercially available, for example, from Sigma-Aldrich (St. Louis, Mo.) or Invitrogen (Carlsbad, Calif.).

The terms "receptor" and "ligand" are used herein for semantic clarity in identifying binding partners and are intended to be interchangeable, unless explicitly indicated to the contrary. Accordingly, the term "receptor" is intended to mean a molecule that is capable of selectively binding a ligand and the term "ligand" is intended to mean a molecule that is capable of selectively binding a receptor. The terms are intended to encompass receptors or ligands that have other functions as well. However, the terms are not intended to be limited by any other function unless indicated otherwise. For example, a receptor can be a naturally occurring polypeptide having signal transducing activity or a functional fragment thereof that exhibits selective binding to a ligand whether or not the functional fragment has signal transducing activity.

As used herein, the term "array" refers to a population of different probe molecules that are attached to one or more substrates such that the different probe molecules can be differentiated from each other according to their relative location. An array can include different probe molecules that are each located at a different addressable location on a substrate. Alternatively, an array can include separate substrates each bearing a different probe molecule, wherein the different probe molecules can be identified according to the locations of the substrates on a surface to which the substrates are attached or according to the locations of the substrates in a liquid such as a fluid stream.

Description of Particular Embodiments

The invention provides a method of determining activity of a protease. The method can include the steps of (a) providing a protease substrate having a protein moiety attached to a nucleic acid moiety; (b) contacting the protease substrate with a protease under conditions wherein the protease catalyzes cleavage of the protein moiety, thereby producing a proteolytic product wherein the nucleic acid moiety is separated from the protein moiety; (c) contacting the proteolytic product with a nucleic acid probe under conditions wherein the nucleic acid moiety hybridizes to a complementary sequence of the probe; and (d) detecting hybridization of the proteolytic product to the probe, thereby determining activity of the protease.

A method of the invention can be used to determine a protease activity that is indicative of the presence of the protease in a sample. Accordingly, the invention can be used to determine the presence or absence of a protease in a sample. For example, a protease substrate having a known or determinable amino acid sequence can be contacted with a sample in a method of the invention and cleavage of the substrate detected. Cleavage, thus, indicates that the sample includes a protease that recognizes the substrate.

An activity of a protease determined in a method of the invention can include one or more characteristic of the protease. For example, the amino acid sequence of a substrate cleaved in a method of the invention can be determined and, if desired, the location where cleavage occurs can also be identified. Such evaluations can be used to determine specificity of a protease for a particular amino acid sequence. The amino acid recognition sequence identified in a method of the invention can be a discreet sequence or a consensus sequence, having one or more degenerate position. Other characteristics of a protease that can be determined in a method of the invention include, for example, rate of catalysis, binding affinity for a particular amino acid sequence or effects of particular conditions or agents on catalytic or binding activity of the protease. Exemplary conditions or agents that can be evaluated include activators, inhibitors, other proteases, pH, salt, temperature or the like.

Activity of a protease can be determined qualitatively or quantitatively in a method of the invention. Exemplary qualitative determinations can include, without limitation, identification of substrate specificity; identification of conditions that increase or decrease activity; determination of the presence or absence of activators or inhibitors of the protease; or determination of relative activities between different samples, proteases, substrates or conditions. Quantitative determinations can be made for these or other characteristics for a more precise measure, if desired. For example, a method of the invention can be used to determine the binding affinity of a ptotease for a particular substrate in the form of a thermodynamic constant, such as a dissociation constant. Accordingly, the methods can be used to identify a protease having dissociation constant for a particular substrate that is, for example, less than about $10^{-4}$, $10^{-5}$, $10^{-6}$, $10^{-7}$, $10^{-8}$, $10^{-9}$ $10^{-10}$, $10^{-11}$, or $10^{-12}$ $M^{-1}$. Similarly, an inhibition constant can be determined for a particular inhibitor in the presence of a protease and its substrate. A further quantitative measure that can be determined in a method of the invention is a catalytic rate constant for protein cleavage. Such kinetic and thermodynamic constants can be determined using titration measurements and/or time dependent measurements in accordance with analyses known in the art as described, for example, in Segel, *Enzyme Kinetics: Behavior and Analysis of Rapid Equilibrium and Steady-State Enzyme Systems*, Wiley, John & Sons, Incorporated (1994).

A method of the invention can be used to determine activity for a sequence-specific protease that recognizes a particular amino acid sequence and cleaves a protein having that sequence as set forth above. Alternatively or additionally, the invention can be used to determine activity for a non-sequence specific protease that is promiscuous with regard to the amino acid sequences it will recognize and cleave. Proteases, whether specific or promiscuous, are involved in several important physiological processes. By providing for determination of protease activity the invention further allows for identification or characterization of one or more physiological processes involving the protease. For example, determination of a protease activity involved with pathogenesis can provide valuable information for identifying or characterizing host-pathogen interactions. Such information can lead to diagnostic or prognostic information. Further examples of physiological processes that can be characterized or identified using a method of the invention include, but are not limited to, blood coagulation, inflammation, programmed cell death (apoptosis), reproduction, fibrinolysis, cancer, the cell cycle, transcriptional regulation, the secretory pathway, cellular stress response or immune response (for example, antigen presentation by MHC molecules during the T-cell immune response).

The ability to perform a multiplexed protease assay in accordance with the invention provides an advantage for the evaluation of protease cascades, signal transduction cascades or other biochemical pathways that are influenced by multiple proteases. A multiplexed protease assay can more closely mimic the complexities of biological systems such that evaluation of the results can yield observations and information that is different or absent when the results of individual assays, using the components of the multiplexed assay, are evaluated alone or in combination.

A substrate useful in the invention can have a protein moiety attached to a nucleic acid moiety in any of a variety of configurations wherein a protease is capable of cleaving the protein moiety. In particular embodiments, a protein moiety is attached to a nucleic acid moiety in a linear arrangement such that the nucleotide at the 3' or 5' end of the nucleic acid moiety is attached to the amino acid at the carboxy or amino terminal residue of the protein moiety. Alternatively, the two moieties can be attached such that an internal amino acid of the protein moiety is attached to the nucleic acid moiety and/or an internal nucleotide of the sequence of the nucleic acid moiety is attached to the protein moiety.

Attachment of a protein moiety and nucleic acid moiety is typically mediated by at least one covalent bond. An attaching bond can be made to any desired portion of a protein moiety including, without limitation, a backbone carbon, nitrogen or oxygen or a sidechain ("R") group. Similarly, a bond can be made to any desired portion of the nucleic acid moiety including, but not limited to, the backbone or base. In the exemplary case where DNA or RNA is used, an attaching bond can be made to the phosphodiester backbone, the sugar moiety or the base. If DNA or RNA analogs, such as those set forth above, are used then a covalent bond used for attachment can be made to known structural moieties therein. Attachment of a PNA-based nucleic acid moiety to a protein moiety is particularly convenient since both moieties contain a similar backbone structure. More specifically, the two moieties can be attached via a peptide bond between the terminal alpha carbonyl of one moiety and terminal alpha amino of the other moiety. PNA or peptide-PNA chimaeras can be synthesized using methods known in the art as described, for example, in U.S. Pat. No. 6,713,602 or Nielsen et al. *Science* 254:1497-1500 (1991).

Figure 2:
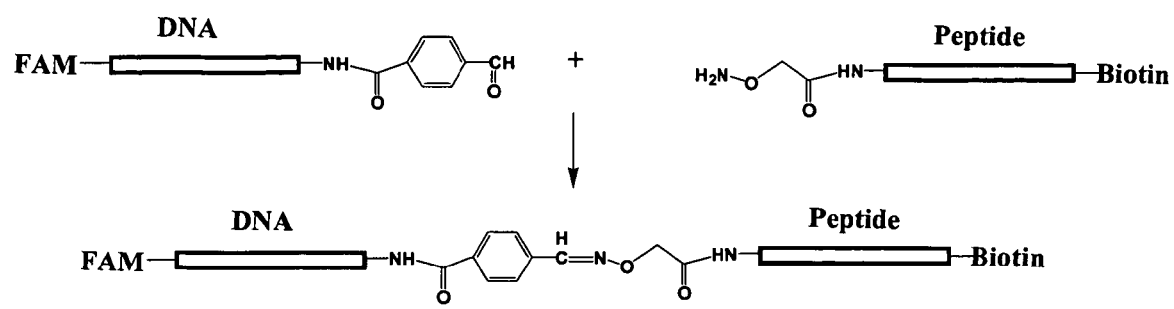
FIG. 2 shows a second method for attaching a DNA moiety to a protein moiety.

Exemplary methods for attaching a DNA moiety to a protein moiety are shown in FIGS. 1 and 2. A DNA molecule having a benzaldehyde nucleotide at the 3' end can be synthesized using methods known in the art such as those described in U.S. Ser. No. 10/739,959. The benzaldehyde residue on the DNA can be coupled to a hydrazine moiety on the amino terminus of a protein to form a hydrazone bond as shown in FIG. 1. Coupling to form the hydrazone bond can be carried out at pH between 4.0 and 7.0. In an alternative method, the benzaldehyde residue on the DNA can be coupled to an aminooxyacetic moiety on the amino terminus of a protein to form an oxime bond as shown in FIG. 2. Coupling to form the oxime bond can be carried out at pH between 4.0 and 5.5. The locations for the reactive moieties on the nucleic acid and protein reactants are provided for purposes of illustration. It will be understood that in order to accommodate various uses of the reagents, the reactive moieties can be placed at locations other than those shown in the Figures or that the reagents can be swapped with each other such that, for example, the protein contains a benzaldehyde moiety and the nucleic acid contains an aminooxyacetic moiety. Furthermore other reactive aldehydes, hydroxylamines and/or hydrazines can be used in place of those exemplified above.

Other pairs of reactive moieties that can be used to couple a protein and nucleic acid molecule to form a protein-nucleic acid conjugate include, for example, Thiol and bromoacetyl, which can be reacted to form a thialkyl linkage; thiol and maleimide which can be reacted to form a maleimide-thioalkyl linkage; aldehydes and cysteine, which can be coupled to form a triazolidine linkage, for example, at pH 2.0 to 8.0; aldehydes and serine, which can be coupled to form an oxazolidine linkage. These and other methods that can be used to synthesize nucleic acid-protein conjugates are described, for example, in Zubin et al., *Russian Chemical Reviews* 71:239-264 (2002) or Tung et al., *Bioconjugate Chemistry* 11:605-618 (2000).

In the exemplary substrate configurations shown in FIGS. 1 and 2, separate label moieties are attached to the ends of the protein moiety and nucleic acid moiety, respectively. As set forth in further detail below, a label can be attached to a portion of a nucleic acid-protein conjugate in a configuration that allows the label to be separated from the nucleic acid moiety upon proteolysis of the conjugate. Alternatively or additionally, a label can be attached to a portion of a nucleic acid-protein conjugate in a configuration that allows the label to be separated from a portion of the protein moiety upon proteolysis of the conjugate. For example, an alternative configuration can include a protein moiety having two attached labels, wherein a first label is attached to a first location of the protein moiety and a second label attached to a second location of the protein moiety and a site in the protein moiety that is capable of being cleaved by a protease occurs between the locations of the two labels. In this case, a nucleic acid moiety can be attached to the protein moiety such that the location of the first label occurs between the nucleic acid moiety and the protease recognition site. Cleavage of the nucleic acid-protein conjugate at the protease recognition site will result in a first fragment containing the nucleic acid moiety and first label, and a second fragment containing a portion of the protein moiety and the second label.

Attachment between a nucleic acid moiety and protein moiety can also be mediated by non-covalent bonds. For example, each moiety can include a partner capable of forming a receptor-ligand complex such as avidin & biotin or other pairs known in the art such as those set forth previously herein.

Figure 3:
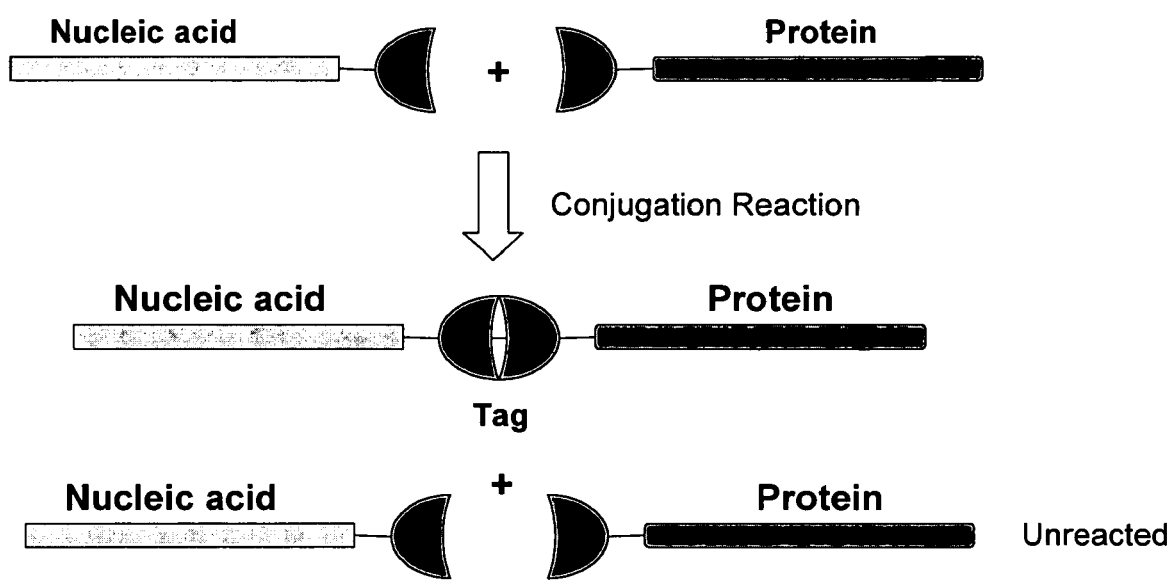
FIG. 3 shows a diagrammatic example of a protease substrate having a nucleic acid moiety (oligonucleotide) and a protein moiety (peptide) attached via a linker having a label (tag).

Attachment between the protein and nucleic acid moieties of a substrate can be mediated by a linker that further includes a primary or secondary label. The use of a linker having a label can provide the non-limiting advantage of allowing detection of the substrate or isolation of the substrate, for example, during synthesis. In a particular embodiment, a linker can include a label that is produced when an appropriate substrate is synthesized. If reactants, undesired reaction side products or both lack the label then the label can be used in order to separate the desired product from other reaction components or to monitor reaction progress or yield. A diagrammatic example of a substrate having a nucleic acid moiety (oligonucleotide) and a protein moiety (peptide) attached via a linker having a label (tag) is shown in FIG. 3. As shown in the figure, unreacted oligonucleotide and peptide reagents have portions of the tag that are not functional. However, correct conjugation to form the desired substrate yields a product having a functional tag that can be used to detect the substrate or isolate it from other reaction components.

Figure 4:
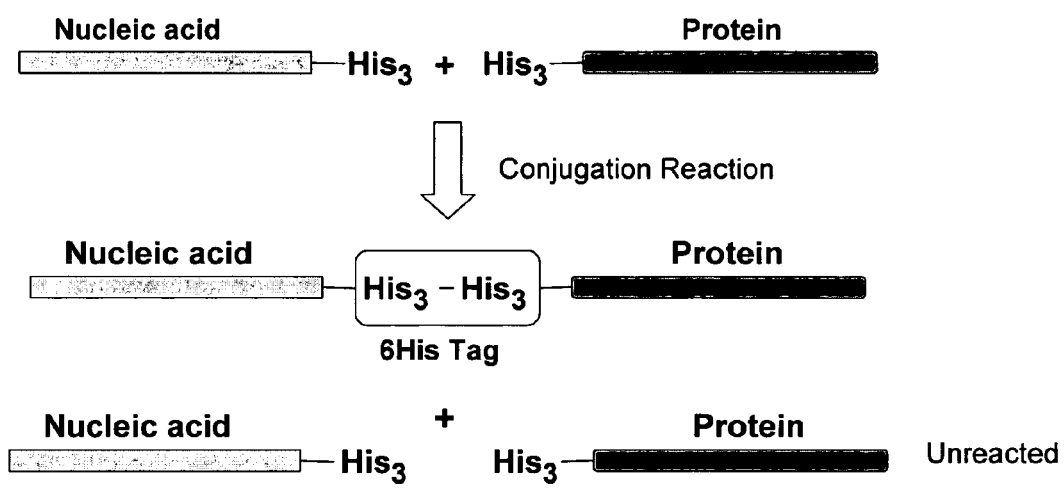
FIG. 4 shows a diagrammatic example of a protease substrate having a nucleic acid moiety (oligonucleotide) and a protein moiety (peptide) attached via a polyhistidine linker that serves as a label.

A first example of a substrate having a labeled linker and its use for separating the substrate from a reaction mixture is shown in FIG. 4. As shown in the figure, the nucleic acid (oligonucleotide) and protein (peptide) moieties each contain a trihistidine sequence. Upon successful conjugation, the trihistidines are directly linked to form a substrate having a nucleic acid moiety and a protein moiety attached via a hexahistidine linker. Isolation of the substrate from other reaction components can be achieved using solid-phase extraction or chromatography with immobilized metal ion media such as $Ni^{2+}$ Sepharose. In this case, separation can occur by exploiting the substantially stronger affinity of $Ni^{2+}$ Sepharose for hexahistidine compared to trihistidine. Similarly, reactants having dihistidines can be used such that the reaction product forms a tetrahistidine label that can be separated from reactants based on higher affinity of $Ni^{2+}$ Sepharose for tetrahistidine compared to dihistidine. Separation of substrates based on the presence of polyhistidine labels can be carried out using methods known in the art as described, for example, in U.S. Pat. Nos. 4,569,794, 5,310, 663, 4,877,830, 5,047,513, or 5,284,933; Hochuli et al., *J. Chromatography* 411:117-184 (1987); or product literature from suppliers of histidine tag reagents such as Qiagen.

Other protein based labels that can be used in the invention, such as in a linker, include, for example, Arg-tag, calmodulin-binding peptide, cellulose-binding domain, DsbA, c-myc-tag, glutathione S-transferase, FLAG-tag, HAT-tag, maltose-binding protein, NusA, S-tag, SBP-tag, Strep-tag, and thioredoxin. Protein and nucleic acid reactants to be conjugated can each have inactive portions of the above tags such that a complete functional label is present in the properly conjugated linker. The resulting labels can be used under separation or detection conditions known in the art as described, for example, in Terpe, *Appl. Microbiol. Biotechnol.* 60:523-533 (2003). Furthermore, those skilled in the art will recognize that such labels can be used as secondary labels in other embodiments set forth herein such as detection of substrates in an array or other format.

Other labels that can be used in the invention, for example, in a linker between a protein moiety and nucleic acid moiety include, for example, a nucleic acid sequence or an epitope for an antibody. In embodiments wherein a nucleic acid-based label is used, detection can be carried out using a complementary probe having higher affinity for the complete label sequence when present in the joined linker compared to its component portions present separately in the protein and nucleic acid moieties. Exemplary epitopes that can be useful include, without limitation, a nucleic acid sequence containing inosine or other base analog or an amino acid sequence having a non-natural amino acid or modification. Again, precursors of the label can be present on reactants such that a desired product having a protein moiety and nucleic acid moiety attached by a linker containing the label can be detected or isolated via the label.

A protease and protease substrate can be contacted under conditions wherein the protease cleaves the substrate. Typically, the reaction is carried out in an aqueous solvent. Protease and protease substrate can be added to a reaction vessel in any order, for example, the protease can be added to a reaction vessel containing the substrate, the substrate can be added to a reaction vessel containing the protease or both can be added simultaneously. Accordingly, addition of one or more components to a protease reaction can be used to initiate the reaction at a defined time. This can be particularly useful for time-based measurements such as those used in kinetic assays. It will be understood that addition of a component to a reaction can include initial physical contact of the component with other components of the reaction or activation of the component from an inactive or sequestered state. For example, a reaction component, such as a substrate or protease, can be present in a caged state by sequestration with another agent. As a further example, a reaction component can be in a non-reactive form and converted to an active form to initiate a reaction. For example, a pro-protease, having a terminal inhibitory sequence, can be initially present in a reaction vessel and then activated by removal of the inhibitory sequence to initiate the protease reaction. Furthermore, a reaction component, such as a protease or substrate, can be activated by addition or removal of a modification such as a phosphate, methyl, acetyl, oligosaccharide, sulfate, poly(ADP-ribose), or isoprenyl (for example, farnesyl or geranylgeranyl) moiety. Accordingly, a method of the invention can be used to determine the effect of such modifications on protease activity, or in turn, to identify agents that alter modification state of a protease or protease substrate.

Components other than protease and substrate can be present in a reaction if desired including, for example, a pH buffer, salt, reducing agent, agent for increasing viscosity or protease inhibitor. A protease inhibitor can be present for the purpose of determining its effect on the activity of a protease of interest with a particular substrate. Alternatively, an inhibitor can be present in a reaction to prevent unwanted activity of one or more proteases other than the protease of interest. Furthermore, conditions can be selected to favor specificity of a protease of interest for a particular substrate or to increase overall activity of the protease for several substrates. Those skilled in the art will know or be able to determine appropriate conditions for protease cleavage according to that which is known in the art as described, for example, in Coligan et al., *Current protocols in Protein Science*, John Wiley and Sons, Baltimore, Md. (2000) or Barrett et al., *Handbook of Proteolytic Enzymes*, Elsevier, Amsterdam, The Netherlands (2004).

A method of the invention can include one or more steps that are carried out using liquid-phase or solid-phase conditions or both. More specifically, a protease and substrate can be contacted under a liquid-phase or solid-phase conditions or both. As an example of a liquid-phase step, a soluble protease can be contacted with a soluble protease substrate under conditions wherein the substrate is cleaved by the protease. A solid-phase step can then ensue, such as capture of the substrate or a proteolytic product of the reaction on a solid-phase support. The solid-phase support can have a receptor that is specific for the substrate, proteolytic product or both. If desired, substrate and proteolytic product can be captured by different receptors that are spatially distinguishable on one or more solid supports. In a further exemplary embodiment, a soluble protease can be contacted with a protease substrate attached to solid-phase support under conditions wherein the substrate is cleaved and soluble proteolytic product is released. The proteolytic product can include a label such that proteolysis is detected as a loss of signal as set forth in further detail below. In particular embodiments, the proteolytic product can be detected in solution or by capture with a second solid-phase support. It is also possible to attach, on a solid-phase support, a protease or other reaction component described herein and use the support in a method of the invention.

In embodiments, including attachment of a protease substrate or other agent to a solid support, the solid support can be selected, for example, from those described herein with respect to detection arrays. Particularly useful substrates include, for example, magnetic beads which can be easily introduced to a reaction mixture and easily removed with a magnet. Other known affinity chromatography substrates can be used as well. Known methods can be used to attach a nucleic acid or protein moiety to a solid support including, for example, this described in U.S. patent application Ser. Nos. 10/651,568 or 10/739,959, WO 01/41918, or WO 04/001646.

A nucleic acid probe can be contacted with a nucleic acid moiety for a substrate or its proteolytic product under conditions wherein the nucleic acid moiety hybridizes to the probe. A variety of hybridization conditions can be used in the present invention, such as high, moderate or low stringency conditions including, but not limited to those described in Sambrook et al., *Molecular Cloning: A Laboratory Manual*, 3rd edition, Cold Spring Harbor Laboratory, New York (2001) or in Brent et al., *Current Protocols in Molecular Biology*, John Wiley and Sons, Baltimore, Md. (2003). Stringent conditions favor specific sequence-dependent hybridization. In general, longer sequences and increased temperatures favor specific sequence-dependent hybridization. A useful guide to the hybridization of nucleic acids is found in Tijssen, *Techniques in Biochemistry and Molecular Biology—Hybridization with Nucleic Acid Probes*, "Overview of principles of hybridization and the strategy of nucleic acid assays" (1993).

A probe used in a method of the invention can include a complementary sequence that is any length capable of binding to a nucleic acid moiety. The complementary sequences can include all or a portion of the probe or nucleic acid moiety. Relatively short complementary sequences can be useful including, for example, those that are at most 5, 6, 7, 8, 9, 10, 11, 12, 13, 14, 15, 16, 17, 18, 19, 20, 25, 30, 35, 40, 50, 60, 70, 80, 90, or 100 nucleotides in length. Those skilled in the art will recognize that specificity of hybridization is generally increased as the length of the complementary sequences is increased. Accordingly, complementary sequences used in a method of the invention can be at least 5, 6, 7, 8, 9, 10, 11, 12, 13, 14, 15, 16, 17, 18, 19, 20, 25, 30, 35, 40, 50, 60, 70, 80, 90, or 100 or more nucleotides long. Those skilled in the art will recognize that a nucleic acid primer used in the invention can also have any of the exemplary lengths set forth above. However, probes and primers useful in the invention can have lengths other than those exemplified above, if desired.

Hybridization steps used in the invention are generally carried out under stringency conditions which selectively allow formation of a hybridization complex in the presence of complementary sequences. Stringency can be controlled by altering a step parameter that is a thermodynamic variable, including, but not limited to, temperature, formamide concentration, salt concentration, chaotropic salt concentration, pH, organic solvent concentration, or the like. These parameters can also be used to control non-specific binding, as is generally outlined in U.S. Pat. No. 5,681,697. Thus, if desired, certain steps can be performed under relatively high stringency conditions to reduce non-specific binding.

Generally, high stringency conditions include temperatures that are about 5-10° C. lower than the thermal melting point ($T_m$) for the annealing sequences at a particular ionic strength and pH. High stringency conditions include those that permit a first nucleic acid to bind a complementary nucleic acid that has at least about 90% complementary base pairs along its length and can include, for example, sequences that are at least about 95%, 98%, 99% or 100% complementary. Stringent conditions can further include, for example, those in which the salt concentration is less than about 1.0 M sodium ion (or other salts), typically about 0.01 to 1.0 M concentration at pH 7.0 to 8.3 and the temperature is at least about 30° C. for short annealing sequences (e.g. 10 to 50 nucleotides) and at least about 60° C. for long annealing sequences (e.g. greater than 50 nucleotides). High stringency conditions can also be achieved with the addition of helix destabilizing agents such as formamide. High stringency conditions can include, for example, conditions equivalent to hybridization in 50% formamide, 5×Denhart's solution, 5×SSPE, 0.2% SDS at 42° C., followed by washing in 0.1×SSPE, and 0.1% SDS at 65° C. Nucleic acid hybrids can be further stabilized by covalent li9nkage between strands using one or more cross-linking agents.

Moderately stringent conditions include those that permit a first nucleic acid to bind a complementary nucleic acid that has at least about 60% complementary base pairs along its length. Depending upon the particular conditions of moderate stringency used, a hybrid can form between sequences that have complementarity for at least about 75%, 85% or 90% of the base pairs along the length of the hybridized region. Moderately stringent conditions include, for example, conditions equivalent to hybridization in 50% formamide, 5×Denhart's solution, 5×SSPE, 0.2% SDS at 42° C., followed by washing in 0.2×SSPE, 0.2% SDS, at 65° C.7

Low stringency hybridization includes, for example, conditions equivalent to hybridization in 10% formamide, 5×Denhart's solution, 6×SSPE, 0.2% SDS at 42° C., followed by washing in 1×SSPE, 0.2% SDS, at 50° C. Denhart's solution and SSPE are well known to those of skill in the art as are other suitable hybridization buffers (see, for example, Sambrook et al., supra (2001) or Brent et al., supra (2003)).

A probe can be hybridized to a nucleic acid moiety of a protease substrate or proteolytic product to distinguish the substrate or proteolytic product from other components of a proteolysis reaction. The probe can be distinguished based on known or determinable characteristics such as spatial or temporal location in a collection of probes or other environment, nucleic acid sequence, presence of a particular label or the like. For example, a probe can be attached to a solid-phase support such that the location of the solid-phase support or location of the probe on the solid-phase support can be used to distinguish the protease substrate or proteolytic product. For example, a solid-phase particle having an attached probe can be distinguished according to its location on a surface such as an array of particles or according to its location in a fluid stream such as in a flow cytometer. In another example, a probe attached at a discrete location on a solid-phase support, such as an array of probes, can be distinguished according to its location on the solid-phase support. In the foregoing examples, a protease substrate or proteolytic product of the invention can be distinguished according to its interaction with a particular probe. Such interactions can be detected according to methods set forth in detail below, such as detection of a label added to the probe, protease substrate or proteolytic product of a hybrid or detection of a physical property of such a hybrid.

Figure 5:
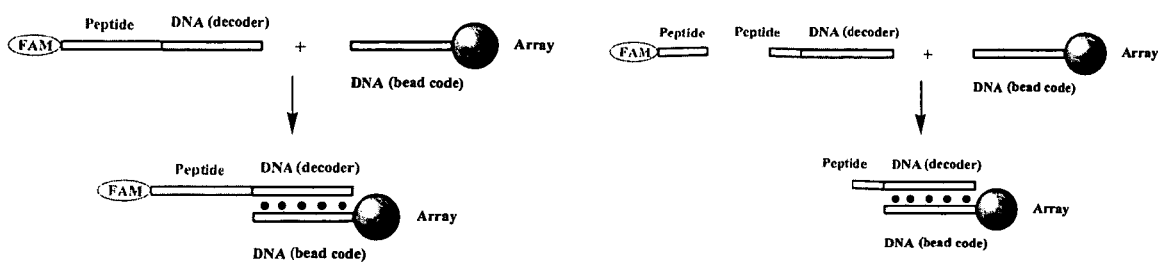
FIG. 5 shows a protease substrate having a protein moiety attached to a FAM label via its amino terminal residue and attached to the 5' end of a DNA moiety via its carboxy-terminal residue; the substrate is shown in a method in which protease activity results in decreased signal for the proteolytic product compared to the protease substrate when each is bound to a nucleic acid probe having a nucleic acid sequence complementary to the DNA moiety.

A label moiety can be attached to a protease substrate of the invention in a configuration that allows the substrate to be distinguished from a proteolytic product of the substrate. For example, when a substrate having a nucleic acid moiety and protein moiety is used in a method of the invention, a label moiety can be attached to the protein moiety such that proteolysis of the substrate produces a proteolytic product wherein the nucleic acid moiety is separated from the label moiety. Protease activity can thus be determined based on detection of the nucleic acid moiety absent the label. An exemplary embodiment is shown in FIG. 5 in which the amino terminal end of a protein moiety is attached to a FAM label and the carboxy-terminal end of the protein moiety is attached to the 5' end of a DNA moiety. As shown in the Figure, protease activity results in separation of the FAM label from the fragment having the DNA moiety. Thus, protease activity can be determined according to an absence of signal or loss of signal on a solid-phase attached probe that is complementary to the nucleic acid moiety. It will be understood that other nucleic acids, labels or both, such as those set forth elsewhere herein, can be attached to a protein moiety in the orientation shown in FIG. 5.

Although the example of FIG. 5 describes a protein moiety having a nucleic acid moiety and label moiety attached at either end, it will be understood that the nucleic acid moiety, label or both can be attached at different locations along the length of the protein moiety. In such embodiments, the substrate and product can be distinguished so long as protease activity separates the nucleic acid and label moieties. Furthermore, another nucleic acid moiety, label or both can be used in a protease substrate having the configuration exemplified in FIG. 5.

In particular embodiments, a label moiety can be attached to the nucleic acid moiety of a protease substrate. The label can be used to determine whether or not the nucleic acid moiety has attached to a complementary nucleic acid probe, for example, as a control to evaluate hybridization conditions. Such a substrate having a label moiety attached to the nucleic acid moiety can also be useful to determine whether or not proteolysis has occurred by determining whether or not the label is present on a receptor, such as an antibody, that binds to the protein moiety. For example, both the antibody and nucleic acid moiety can be attached to different label moieties such that the presence of both labels indicates absence of proteolytic activity whereas the presence of the antibody-attached label moiety and absence of the nucleic acid-attached label moiety indicates presence of proteolytic activity. Similarly, presence or absence of the nucleic acid-attached label moiety on a particular antibody bearing particle or at a particular location on an antibody bearing surface can be detected to determine absence or presence of proteolytic activity, respectively. Although the examples above and elsewhere in the specification refer to absence of proteolytic activity, it will be understood that absence of proteolysis can be characterized by low levels of substrate cleavage so long as they are not substantial or statistically relevant compared to levels detected or expected for actual proteolytic activity. Furthermore, methods similar to those exemplified above can be used to determine a decrease in proteolytic activity, for example, in the presence of a protease inhibitor.

As set forth above and elsewhere herein, a label moiety that is not a natural component of nucleic acids or proteins found in nature, thus exogenous to these molecules, can be used in a method of the invention. However, it will be understood that a substrate and/or proteolytic product used in a method of the invention need not have an exogenous label moiety. In an embodiment wherein a substrate having a nucleic acid moiety and protein moiety is used in a method of the invention, the protease substrate can be distinguished from the proteolytic product due to the presence or absence, respectively, of a receptor that binds the protein moiety when the nucleic acid moiety is hybridized to a complementary nucleic acid probe. A particularly useful receptor is an antibody that binds specifically to the amino acid sequence of the proteolytic substrate. Alternatively, presence or absence of the protein moiety can be determined based on chemical detection methods including, for example, non-specific chemical methods such as ninhydrin staining or colorometric stains like Coomassie blue or silver stain. If desired, sequence-specific chemical methods such as amino acid sequencing can be used to detect presence or absence of a protein moiety in a protease substrate or proteolytic product.

Exemplary primary and secondary labels that can be used in a method of the invention are set forth above in the definitions section. Other labels can be used as well. Secondary labels can be useful for attaching a protease substrate or proteolytic product or other agent to a solid-phase support. Secondary labels that can be used include receptors or ligands. Exemplary pairs of ligands and receptors that can be used in the invention include, without limitation, antigen & immunoglobulin or active fragments thereof, such as FAbs; immunoglobulins from different organisms or of different subtype that bind each other (or active fragments); avidin & biotin, or analogs thereof having specificity for avidin such as imino-biotin; streptavidin & biotin, or analogs thereof having specificity for streptavidin; complementary nucleic acid molecules; or carbohydrates & lectins. It will be understood that either partner in the above-described pairs can be attached to a protease substrate, proteolytic product solid-phase support or other agent useful in the invention. It will be further understood that several useful label moieties can function as both primary and secondary labels in a method of the invention. For example, strepatvidin-phycoerythrin can be detected as a primary label due to fluorescence from the phycoerythrin moiety or it can be detected as a secondary label due to its affinity for anti-streptavidin antibodies.

In a particular embodiment, a secondary label can be a chemically modifiable moiety. In this embodiment, labels having reactive functional groups can be incorporated into a protease substrate, proteolytic product or other agent useful in the invention. The functional group can be subsequently covalently reacted with a primary label. Suitable functional groups include, but are not limited to, amino groups, carboxy groups, maleimide groups, oxo groups and thiol groups.

Secondary labels can be particularly useful when attached to protease substrates or proteolytic products because they can be attached to an array via these labels. Furthermore, secondary labels can be useful for separating unreacted protease substrates or proteolytic products from other components of a protease reaction, or detecting these molecules when bound to probes, for example, in an array.

A label moiety can be attached to a protease substrate or other agent useful in the invention using methods known in the art. For example, a label moiety can be attached to a base, ribose, phosphate, or analogous structure of a nucleic acid moiety. In particular embodiments, a moiety can be incorporated using modified nucleosides that are added to a growing nucleotide strand, for example, during a detection step that includes modification of a probe or hybridized nucleic acid moiety, as set forth in further detail below. Nucleosides can be modified, for example, at the base, phosphate or the ribose. Analogous structures can be modified in a nucleic acid analog in order to attach a label moiety.

A method of the invention can further include a step of detecting hybridization of a probe to a target molecule such as a protease substrate or proteolytic product. Depending upon the particular application of the invention, a probe-target hybrid can be detected using a direct detection technique, or alternatively an amplification-based technique. Direct detection techniques include those in which the level of nucleic acids in probe-fragment hybrids provides the detected signal. For example, in the case of a hybrid formed at a particular array location, the signal from the location arising from the resident hybrid or one of its component nucleic acids can be detected without amplifying the hybrid or its component nucleic acids. Alternatively, detection can include amplification of the probe or target or both to increase the level of nucleic acid that is detected.

As set forth below in the context of various exemplary detection techniques, a probe, nucleic acid moiety of a target molecule or both can be labeled. Furthermore, nucleic acids in a probe-target hybrid can be labeled prior to, during or after hybrid formation and determination of protease activity based on detection of such labels.

Generally, detection, whether direct or based on an amplification technique, can be achieved by methods that perceive properties that are intrinsic to a nucleic acid or a label associated with the nucleic acid. Useful properties include, those that can be used to distinguish different nucleic acids alone, or in combination with other methods, such as attachment of the nucleic acids to solid-phase supports. Exemplary properties upon which detection can be based include, but are not limited to, mass, electrical conductivity, energy absorbance, fluorescence, magnetism, luminescence or the like.

Detection of fluorescence can be carried out by irradiating a protease substrate, proteolytic product or label moiety with an excitatory wavelength of radiation and detecting emitted radiation by methods known in the art and described for example in Lakowicz, *Principles of Fluorescence Spectroscopy*, 2nd Ed., Plenum Press New York (1999). A fluorophore can be detected based on any of a variety of fluorescence phenomena including, for example, emission, excitation, fluorescence resonance energy transfer (FRET) intensity, quenching, anisotropy or lifetime at one or more wavelengths. FRET can be used to identify hybridization between a probe bearing a donor fluorophore and a target bearing an acceptor fluorophore due to transfer of energy from the excited donor to the acceptor. Donor and acceptor can be on target and probe, respectively, as well. In either case, hybridization can be detected as a shift in wavelength maximum, reduction of donor emission or appearance of acceptor emission for the hybrid.

Other detection techniques that can be used to detect a protease substrate or ptoteolytic product include, for example, mass spectrometry which can be used to perceive a molecule or complex based on its mass; surface plasmon resonance which can be used to perceive a molecule or complex based on binding or dissociation from a surface; absorbance spectroscopy which can be used to perceive a molecule or complex based on the wavelength of the energy it absorbs; calorimetry which can be used to perceive a molecule or complex based on changes in temperature of its environment upon binding or dissociation; electrical conductance or impedance which can be used to perceive a molecule or complex based on changes in its electrical properties or in the electrical properties of its environment; magnetic resonance which can be used to perceive a molecule or complex based on presence of magnetic nuclei; or other known analytic spectroscopic or chromatographic techniques.

In particular embodiments, a probe-target hybrid can be detected based on the presence of the probe, target or both in the hybrid, without subsequent modification of the hybrid species. For example, a pre-labeled target can be identified based on presence of the label at a particular array location where a complementary probe resides.

Alternatively or additionally, a nucleic acid probe can be modified while hybridized to a target and the modification detected in a method of determining protease activity. Similarly, a nucleic acid moiety in a target that is hybridized to a probe can be modified. In embodiments wherein one or more nucleotides is added by an enzyme having polymerase or ligase activity, the probe or target nucleic acid moiety will have a 3' hydroxyl that is accessible. For example, a probe can be attached to a solid-phase support via its 5' end or via another location on the nucleic acid such that the 3' end is free for enzymatic modification. If desired a protease substrate used in the invention can include a nucleic acid moiety that is attached to a protein via its 5' end or via another portion of the nucleic acid such that the 3' end is free for enzymatic modification. Exemplary methods that can be used to modify a nucleic acid, such as a probe or nucleic acid moiety, for detection in accordance with the invention include, for example, those utilizing an extension assay, such as ASPE or SBE; a ligation assay such as oligonucleotide ligation; an assay including extension and ligation (such as the GoldenGate™ assay of Illumina, Inc.); invader assay; probe cleavage; or pyrosequencing as described, for example, in U.S. Pat. No. 6,355,431 B1 or U.S. patent application Pub. No. 04/0259100.

A plurality of probes can be used in a method of the invention thereby allowing for detection of a plurality of protease substrates or proteolytic products. Accordingly, the invention further provides a method of determining activity of at least one protease. The method can include the steps of (a) providing a plurality of different substrates each having a protein moiety attached to a nucleic acid moiety, wherein the sequence of each nucleic acid moiety is unique to the sequence of a different protein moiety; (b) contacting the substrates with at least one protease under conditions wherein the at least one protease catalyzes cleavage of the protein moieties, thereby producing proteolytic products wherein the nucleic acid moieties are separated from the protein moieties; (c) contacting the proteolytic products with nucleic acid probes under conditions wherein the nucleic acid moieties hybridize to complementary sequences of the probes; and (d) detecting hybridization of the proteolytic products to the probes, thereby determining activity of the at least one protease.

An advantage of the invention is that a plurality of protease reactions can be carried out in a multiplex format. Thus, a method of the invention can be used to determine activity for a plurality of proteases for one or more different substrates, to determine activity of one or more protease for a plurality of different substrates, or to determine the effects of one or more different inhibitors on one or more proteases. Such a plurality of protease reactions can be carried out simultaneously and in the same reaction vessel. However, if desired a plurality of protease assays can be carried out sequentially in the same or different reaction vessels using a method of the invention.

A multiplex reaction can include at least about 2, 3, 4, 5, 8, 10, 15, 20, 24, 30, 40, 48, 50, 60, 70, 80, 90, 96, 100, 200, 300, 386, 400, 500, 1000 or more different protease substrates or suspected protease substrates. The number of proteases can also be multiplexed such that a reaction includes at least about 2, 3, 4, 5, 8, 10, 15, 20, 24, 30, 40, 48, 50, 60, 70, 80, 90, 96, 100, 200, 300, 386, 400, 500, 1000 or more different proteases or suspected protease substrates. A multiplex reaction can include any combination of these exemplary numbers of proteases and protease substrates. Furthermore, a multiplex reaction can be carried out with fewer of each component if desired including, for example, at most about a billion, million, 100,000, 10,000, 1,000, 500, 386, 96, 48, 8 or 5 different proteases, proteases substrates or both (whether known or suspected).

Different protease substrates used in a method of the invention can have different amino acid sequences such that identification of those sequences that are cleaved by a protease, those that are not substantially cleaved by the protease, or both can be used to determine the sequence specificity of the protease. In such embodiments, each different protein moiety can be attached to a nucleic acid moiety having a particular nucleotide sequence. In this way different nucleotide sequences can be correlated with different amino acid sequences allowing convenient identification of which protease substrates are cleaved or not cleaved based on the identity of the nucleotide sequence. For example, the amino acid sequence of a protein-nucleic acid substrate that is recognized by a particular protease can be determined according to the sequence of a nucleic acid probe that hybridizes to the nucleic acid moiety of the substrate or its proteolytic product. An advantage of correlating the nucleotide sequence with a particular protein moiety is that the same label can be attached to several different substrates, for example, in a multiplex protease assay, allowing a plurality of the substrates or their proteolytic products to be detected en masse using uniform detector settings yet distinguished one from the other based on the identity of the nucleic acid probe to which they hybridize. As set forth below, the components of a multiplexed protease assay can be contacted with an array of solid phase probes, and the components distinguished based on detection of the same label at different locations in the array, thereby allowing determination of an activity of one or more proteases in the reaction.

A plurality of nucleic acid probes used in a method of the invention can be included in an array of probes attached to one or more solid support. In particular embodiments, probes useful in detecting protease substrates, proteolytic products or other target molecules can be attached to particles that are arrayed or otherwise spatially distinguished. Exemplary particles include microspheres or beads. It will be understood that particles such as microspheres or beads can be spherical or approximately spherical but need not be perfectly spherical. Rather solid phase particles having other shapes including, but not limited to, cylinders, disks, plates, chips, slivers or irregular shapes can be used. In addition, particles used in the invention can be porous, thus increasing the surface area available for attachment or detection of molecules such as probes or targets. Particle sizes can range, for example, from nanometers such as about 100 nm beads, to millimeters, such as about 1 mm beads, with particles of intermediate size such as at most about 0.2 micron, 0.5 micron, 5 micron or 200 microns being useful. The composition of the beads can vary depending, for example, on the application of the invention or the method of synthesis. Typically, useful particles consist of a substantially non-compressible or inelastic material compared to a biological cell such as plastics, ceramics, glass, polystyrene, methylstyrene, acrylic polymers, paramagnetic materials, thoria sol, carbon graphite, titanium dioxide, latex, Teflon™, cross-linked dextrans such as Sepharose™, cellulose, or nylon. However, if desired a biological cell or similarly compressible particle such as a cross-linked micelle can be used as a solid phase support in the invention. Other suitable bead compositions include, but are not limited to, those used in peptide, nucleic acid and organic moiety synthesis or others described, for example, in *Microsphere Detection Guide* from Bangs Laboratories, Fishers Ind.

Several embodiments including the use of array-based detection in the invention are exemplified below for beads or microspheres. Exemplary bead-based arrays that can be used in the invention include, without limitation, those in which beads are associated with a solid support such as those described in U.S. Pat. No. 6,355,431 B1, U.S. 2002/0102578 and PCT Publication No. WO 00/63437. Beads can be located at discrete locations, such as wells, on a solid-phase support, whereby each location accommodates a single bead. Alternatively, discrete locations where beads reside can each include a plurality of beads as described, for example, in U.S. patent application Ser. Nos. U.S. 2004/0263923, U.S. 2004/0233485, U.S. 2004/0132205, or U.S. 2004/0125424. Beads can be associated with discrete locations via covalent bonds or other non-covalent interactions such as gravity, magnetism, ionic forces, van der Waals forces, hydrophobicity or hydrophilicity. However, the sites of an array of the invention need not be discrete sites. For example, it is possible to use a uniform surface of adhesive or chemical functionalities that allows the attachment of particles at any position. Thus, the surface of an array substrate can be modified to allow attachment or association of microspheres at individual sites, whether or not those sites are contiguous or non-contiguous with other sites. Thus, the surface of a substrate can be modified to form discrete sites such that only a single bead is associated with the site or, alternatively, the surface can be modified such that a plurality of beads populates each site.

Beads or other particles can be loaded onto array supports using methods known in the art such as those described, for example, in U.S. Pat. No. 6,355,431. In some embodiments, for example when chemical attachment is done, particles can be attached to a support in a non-random or ordered process. For example, using photoactivatible attachment linkers or photoactivatible adhesives or masks, selected sites on an array support can be sequentially activated for attachment, such that defined populations of particles are laid down at defined positions when exposed to the activated array substrate. Alternatively, particles can be randomly deposited on a substrate. In embodiments where the placement of probes is random, a coding or decoding system can be used to localize and/or identify the probes at each location in the array. This can be done in any of a variety of ways, for example, as described in U.S. Pat. No. 6,355,431 or WO 03/002979. A further encoding system that is useful in the invention is the use of diffraction gratings as described, for example, in U.S. patent application Ser. Nos. U.S. 2004/0263923, U.S. 2004/0233485, U.S. 2004/0132205, or U.S. 2004/0125424.

An array of beads useful in the invention can also be in a fluid format such as a fluid stream of a flow cytometer or similar device. Exemplary formats that can be used in the invention to distinguish beads in a fluid sample using microfluidic devices are described, for example, in U.S. Pat. No. 6,524,793. Commercially available fluid formats for distinguishing beads include, for example, those used in XMAP™ technologies from Luminex or MPSS™ methods from Lynx Therapeutics.

Any of a variety of arrays known in the art can be used in the present invention. For example, arrays that are useful in the invention can be non-bead-based. A particularly useful array is an Affymetrix® GeneChip® array. GeneChip® arrays can be synthesized in accordance with techniques sometimes referred to as VLSIPS™ (Very Large Scale Immobilized Polymer Synthesis) technologies. Some aspects of VLSIPS™ and other microarray and polymer (including protein) array manufacturing methods and techniques have been described in U.S. Pat. No. 09/536,841, International Publication No. WO 00/58516; U.S. Pat. Nos. 5,143,854, 5,242,974, 5,252,743, 5,324,633, 5,445,934, 5,744,305, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846, 6,022,963, 6,083,697, 6,291,183, 6,309,831 and 6,428,752; and in PCT Applications Nos. PCT/US99/00730 (International Publication No. WO 99/36760) and PCT/US01/04285.

A spotted array can also be used in a method of the invention. An exemplary spotted array is a CodeLink™ Array available from Amersham Biosciences. CodeLink™ Activated Slides are coated with a long-chain, hydrophilic polymer containing amine-reactive groups. This polymer is covalently crosslinked to itself and to the surface of the slide. Probe attachment can be accomplished through covalent interaction between the amine-modified 5' end of the oligonucleotide probe and the amine reactive groups present in the polymer. Probes can be attached at discrete locations using spotting pens. Useful pens are stainless steel capillary pens that are individually spring-loaded. Pen load volumes can be less than about 200 nL with a delivery volume of about 0.1 nL or less. Such pens can be used to create features having a spot diameter of, for example, about 140-160 µm. In a preferred embodiment, nucleic acid probes at each spotted feature can be 30 nucleotides long. However, probes having other lengths such as those set forth elsewhere herein can also be attached at each spot.

An array that is useful in the invention can also be manufactured using inkjet printing methods such as SurePrint™ Technology available from Agilent Technologies. Such methods can be used to synthesize oligonucleotide probes in situ or to attach pre-synthesized probes having moieties that are reactive with a support surface. A printed microarray can contain 22,575 features on a surface having standard slide dimensions (about 1 inch by 3 inches). Typically, the printed probes are 25 or 60 nucleotides in length. However, probes having other lengths such as those set forth elsewhere herein can also be printed at each location.

An exemplary high density array is an array of arrays or a composite array having a plurality of individual arrays that is configured to allow processing of multiple samples. Such arrays allow multiplex detection of protease assays. Exemplary composite arrays that can be used in the invention, for example, in multiplex detection formats are described in U.S. Pat. No. 6,429,027 and U.S. patent application Pub. No. 2002/0102578. In particular embodiments, each individual array can be present within each well of a microtiter plate. Thus, depending on the size of the microtiter plate and the size of the individual array, very high numbers of assays can be run simultaneously; for example, using individual arrays of 2,000 probes and a 96 well microtiter plate, 192,000 assays can be performed in parallel; the same number of probes in each well of a 384 microtiter plate yields 768,000 simultaneous assays, and in a 1536 microtiter plate gives 3,072,000 assays.

In some embodiments, solid-phase attached probes, such as nucleic acids or peptides, can be synthesized by sequential addition of monomer units directly on a solid support used in an array such as a bead or slide surface. Methods known in the art for synthesis of a variety of different chemical compounds on solid supports can be used in the invention, such as methods for solid-phase synthesis of peptides, organic moieties, and nucleic acids. Alternatively probes can be synthesized first, and then covalently attached to a solid support, for example, via reactive functional groups. Functionalized solid supports can be produced by methods known in the art or, if desired, obtained from any of several commercial suppliers. Exemplary surface chemistries that are useful in the invention include, but are not limited to, amino groups such as aliphatic and aromatic amines, carboxylic acids, aldehydes, amides, chloromethyl groups, hydrazide, hydroxyl groups, sulfonates or sulfates. If desired, a probe can be attached to a solid support via a chemical linker. Such a linker can have characteristics that provide, for example, stable attachment, reversible attachment, sufficient flexibility to allow desired interaction with a target molecule to be detected, or to avoid undesirable binding reactions. Further exemplary methods that can be used in the invention to attach polymer probes to a solid support are described in U.S. patent application Ser. Nos. 10/651,568 or 10/739,959; WO 01/41918; WO 04/001646; Pease et al., *Proc. Natl. Acad. Sci. USA* 91(11):5022-5026 (1994); Khrapko et al., *Mol Biol (Mosk) (USSR)* 25:718-730 (1991); Stimpson et al., *Proc. Natl. Acad. Sci. USA* 92:6379-6383 (1995) or Guo et al., *Nucleic Acids Res.* 22:5456-5465 (1994).

Very high density arrays are useful in the invention including, for example, those having from about 10,000,000 array locations/cm$^2$ to about 2,000,000,000 array locations/cm$^2$ or from about 100,000,000 array locations/cm$^2$ to about 1,000,000,000 array locations/cm$^2$. High density arrays can also be used including, for example, those in the range from about 100,000 array locations/cm$^2$ to about 10,000,000 array locations/cm$^2$ or about 1,000,000 array locations/cm$^2$ to about 5,000,000 array locations/cm$^2$. Moderate density arrays useful in the invention can range from about 10,000 array locations/cm$^2$ to about 100,000 array locations/cm$^2$, or from about 20,000 array locations/cm$^2$ to about 50,000 array locations/cm$^2$. Low density arrays are generally less than 10,000 particles/cm$^2$ with from about 1,000 array locations/cm$^2$ to about 5,000 array locations/cm$^2$ being useful in particular embodiments. Very low density arrays having less than 1,000 array locations/cm$^2$, from about 10 array locations/cm$^2$ to about 1000 array locations/cm$^2$, or from about 100 array locations/cm$^2$ to about 500 array locations/cm$^2$ are also useful in some applications.

A solid-phase support used in an array of the invention can be made from any material that can be modified to contain discrete individual sites or to attach a desired probe. In embodiments where arrays of particles are used, a material that is capable of attaching or associating with one or more type of particles can be used. Useful supports include, but are not limited to, glass; modified glass; functionalized glass; plastics such as acrylics, polystyrene and copolymers of styrene and other materials, polypropylene, polyethylene, polybutylene, polyurethanes, Teflon, or the like; polysaccharides; nylon; nitrocellulose; resins; silica; silica-based materials such as silicon or modified silicon; carbon; metal; inorganic glass; optical fiber bundles, or any of a variety of other polymers. Useful supports include those that allow optical detection, for example, by being translucent to energy of a desired detection wavelength and/or do not themselves appreciably fluoresce at particular detection wavelengths.

The surface of a solid-phase support can include a plurality of individual arrays that are physically separated from each other. For example, physical separation can be due to the presence of assay wells, such as in a microtiter plate. Other barriers that can be used to physically separate array locations include, for example, gaskets, raised barriers, channels, hydrophobic regions that will deter flow of aqueous solvents or hydrophilic regions that will deter flow of apolar or hydrophobic solvents.

Arrays that are physically separated from each other provide separate assay locations. An assay location can include an array of probes and provide a vessel for holding a fluid such that the fluid contacts the probes. For example, an assay location containing a multiplex protease reaction can be contacted with an array of probes under hybridization conditions set forth herein or known in the art. Similarly, a wash fluid or fluid containing other reagents or analytes described herein can be contacted with an array of probes when placed in an assay location. An assay location can be enclosed, if desired, for example, to form a hybridization chamber. Exemplary enclosures include, without limitation, a cassette, enclosed well, or a slide surface enclosed by a gasket or membrane or both. Further exemplary enclosures that are useful in the invention are described in WO 02/00336, U.S. patent application Pub. 02/0102578 or the references cited previously herein in regard to different types of arrays.

In a particular embodiment, an array support can be an optical fiber bundle or array, as is generally described in U.S. Ser. No. 08/944,850, U.S. Pat. No. 6,200,737; WO 98/40726; and WO 98/50782. Also useful in the invention is a preformed unitary fiber optic array having discrete individual fiber optic strands that are co-axially disposed and joined along their lengths. A distinguishing feature of a preformed unitary fiber optic array compared to other fiber optic formats is that the fibers are not individually physically manipulable; that is, one strand generally cannot be physically separated at any point along its length from another fiber strand.

In a particular embodiment, several levels of redundancy can be built into an array used in the invention. As will be appreciated by those in the art, there are at least two types of redundancy that can be built into an array: the use of multiple identical probes or the use of multiple probes directed to the same target, but having different chemical functionalities. For example, for the detection of nucleic acids, sensor redundancy utilizes a plurality of sensor elements, such as beads, having identical binding ligands. Target redundancy utilizes sensor elements with different probes to the same target. For example, one probe can span the first 25 bases of a target, a second probe can span the second 25 bases of the target, etc. As will be appreciated by those in the art, the number of redundant probes in a sub-population will vary with the application and use of a particular array. In general, anywhere from 2 to thousands of redundant probes can be used, including, for example, about 5, 10, 20, 50 or 100 probes that are at different locations but otherwise identical or capable of binding the same target molecule.

Building redundancy into an array can give several non-limiting advantages, including the ability to make quantitative estimates of confidence about the data collected from an array. Also redundancy can provide substantial increases in sensitivity due to the ability to sum signals. A variety of statistical mathematical analyses can be done for analysis of large data sets. Exemplary analyses include, but are not limited to, baseline adjustment, averaging, standard deviation analysis, distribution and cluster analysis, confidence interval analysis, mean testing, or the like. Analyses based on redundancy that can be used in the invention are generally described in texts such as Freund and Walpole, *Mathematical Statistics*, Prentice Hall Inc., New Jersey (1980). Other methods for making and using redundant arrays are described, for example, in U.S. Pat. No. 6,355,431 and WO 00/60332. Redundancy can be particularly useful for increasing confidence levels or determining statistical validity for measurements of kinetic or thermodynamic properties of protease activity such as binding constants, maximum velocity, catalytic rate constant or others as described for example, in Segel, *Enzyme Kinetics: Behavior and Analysis of Rapid Equilibrium and Steady-State Enzyme Systems*, Wiley, John & Sons, Incorporated (1994).

Although the invention is exemplified above and elsewhere herein with respect to an array of immobilized probes, those skilled in the art will recognize that other detection formats can be employed as well. For example, the methods set forth herein can be carried out in solution phase rather than solid phase. Accordingly, solution phase probes can replace immobilized probes in the methods set forth herein. Solution phase probes can be detected according to properties such as those set herein in regard to detection labels or detection moieties. For example, probes can have identifiable charge, mass, charge to mass ratio or other distinguishing properties. Such distinguishing properties can be detected, for example, in a chromatography system including, for example, capillary electrophoresis, acrylamide gel, agarose gel or the like, or in a spectroscopic system such as mass spectroscopy.

A method of the invention can include a step of comparing the level of a protease substrate with the level of a proteolytic product derived from the substrate in the presence of a particular protease. Such a comparison can be particularly useful in embodiments where protease activity is indicated by a loss of signal. For example, if an assay is performed in which protease activity is determined based on removal of a label from a protease substrate then loss of signal can occur either due to protease activity or due to an experimental artifact such as poor signal detection, loss of substrate or the like. In this example, detection of the level of protease substrate can be used as a control for experimental artifact by comparing to the level of proteolytic product. Such comparisons can be carried out for pluralities of proteases, protease substrates or proteolytic products or a combination thereof. Thus, a plurality of comparisons can be made with a plurality of protease substrates in accordance with methods set forth herein.

As set forth previously herein, a plurality of different protease substrates useful in a method of the invention can have substantially the same label. In such cases, target molecules can be distinguished based on detection of the label in combination with identification of the nucleotide sequence of the nucleic acid moieties. Such methods are exemplified above based on the use of arrays in which a plurality of target molecules are detected based on signals from the labels and the nucleotide sequence of each is identified based on the location of the target molecules in the array. However, it is also possible to use one or more different labels for a plurality of protease substrates or proteolytic products used in a method of the invention.

Accordingly, a particular target molecule can be identified within a plurality of different target molecules based on the identity of the label alone. Thus, an array need not be used to differentiate a plurality of target molecules in a method of the invention, for example, if a sufficient number of different labels are available to uniquely identify each target molecule.

A multiplex reaction can be carried out under conditions wherein a plurality of different proteases are present and one or more of the proteases is capable of inactivating or inhibiting one or more other proteases present in the same reaction vessel. In such embodiments, control reactions can be carried out in which one or more of the proteases are omitted. Comparison of the protease activity of an analytical reaction containing a full set of proteases with a control reaction omitting one or more of the proteases can be used to evaluate cross reactivity between proteases. Furthermore, one or more protease inhibitors can be added in sufficient concentration to inactivate one or more proteases that are present in a reaction or potentially present in a reaction. Such protease inhibitors can be added to prevent unwanted proteolysis of a protease under investigation or its substrate. Alternatively, varying concentrations of a protease inhibitor can be used to determine if protease cross reactivity is occurring.

The invention further provides for methods in which protease activity can be determined as a gain of signal. For example, the invention provides a method of determining activity of a protease including the steps of (a) providing a substrate having a protein moiety attached to a nucleic acid moiety and a ligand moiety; (b) contacting the substrate with a protease under conditions wherein the protease catalyzes cleavage of the protein moiety, thereby producing a proteolytic product wherein the nucleic acid moiety is separated from the protein moiety and the ligand moiety; (c) contacting the proteolytic product with a receptor under conditions wherein the ligand moiety binds to the receptor to form a complex; (d) separating the complex from the nucleic acid moiety, thereby forming a separation product having the nucleic acid moiety; (e) contacting the separation product with a probe nucleic acid under conditions wherein the nucleic acid moiety hybridizes to a complementary sequence of the probe; and (f) detecting hybridization of the separation product to the probe, thereby determining activity of the protease.

Figure 6:
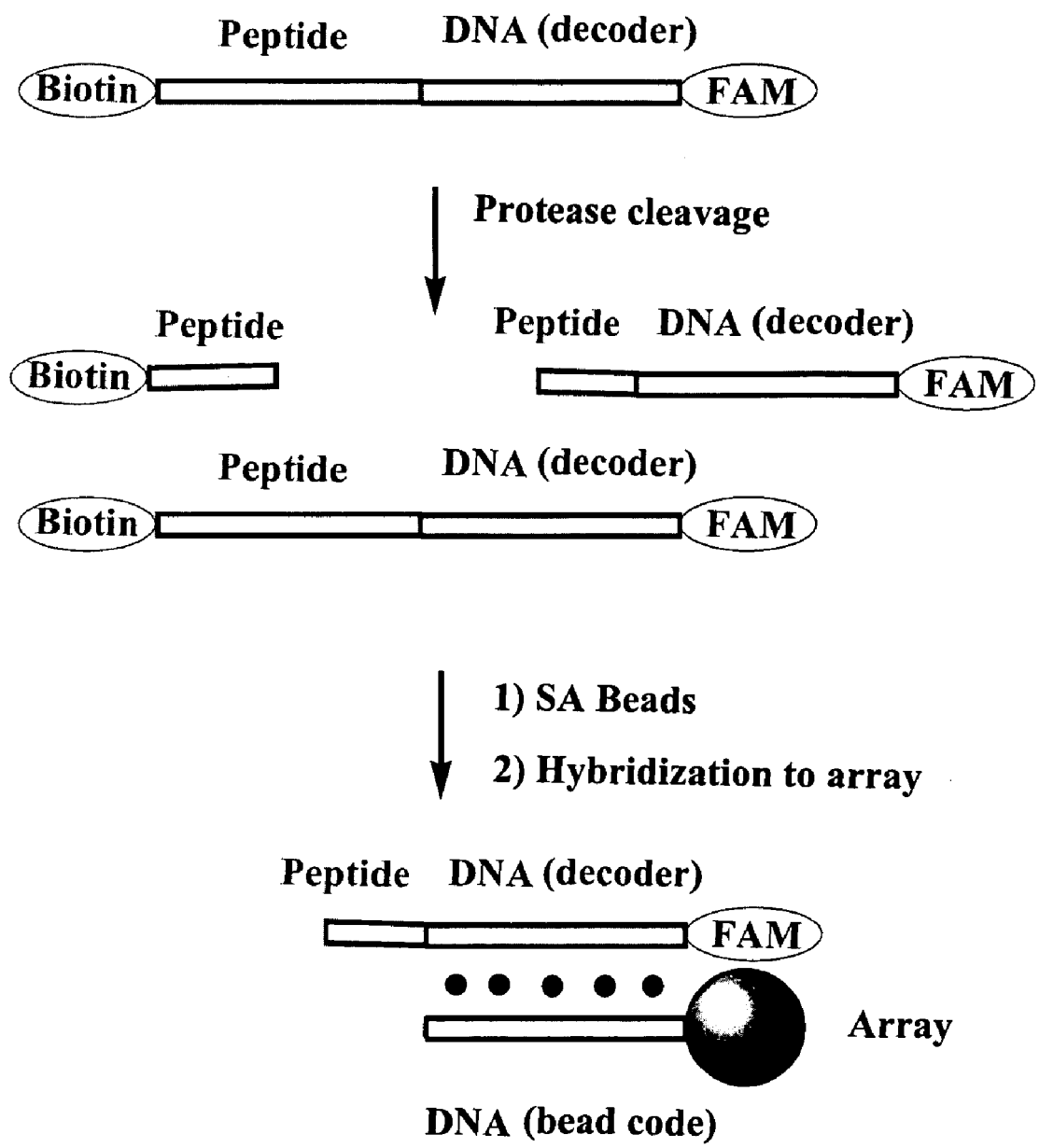
FIG. 6 shows a protease substrate having a protein moiety attached to a biotin label via its amino terminal residue and attached to the 5' end of a DNA moiety via its carboxy-terminal residue, wherein the 3' end of the DNA moiety is attached to a FAM label; the substrate is shown in a method in which protease activity results in increased signal for the proteolytic product compared to the protease substrate when each is bound to a nucleic acid probe having a nucleic acid sequence complementary to the DNA moiety.

An exemplary embodiment wherein a proteolytic product is detected following separation from protease substrate is shown in FIG. 6. The protease substrate shown in the figure has a biotin attached to the amino terminal end of the protein moiety and the carboxy terminal end of the protein moiety is attached to the 5' end of a DNA moiety. Additionally, the 3' end of the DNA moiety is attached to a FAM label. Protease activity results in cleavage of the protein moiety such that the biotin moiety is separated from the FAM labeled DNA moiety. If the protease substrate is not cleaved then the DNA moiety remains attached to the biotin moiety. Support bound streptavidin when contacted with the reaction mixture can bind to the biotinylated protease substrate and the portion of the proteolytic product that lacks the FAM labeled DNA moiety. However, the proteolytic product that has the FAM labeled DNA moiety does not bind to the streptavidin, thereby allowing it to be separated from the uncleaved protease substrate and the other product. The separated proteolytic product is contacted with a solid-phase probe having a sequence that is complementary to the DNA moiety and protease activity is determined according to the presence of FAM signal on the probe. It will be understood that the method exemplified in FIG. 6 can be used with a protease substrate having the nucleic acid moiety, label or both attached at different locations from those shown. In such embodiments, the substrate and product can be distinguished so long as protease activity separates the nucleic acid moiety from the label moiety used for solid phase removal of uncleaved substrate. Furthermore, another nucleic acid moiety, label (in place of FAM or biotin) or combination thereof can be used in a protease substrate having the configuration exemplified in FIG. 6. Examples of other moieties that are useful are set forth previously herein.

Any of a variety of secondary labels can be used to separate protease substrates from proteolytic products. Examples are set forth herein previously. The secondary labels can be attached to a solid-phase support such as a particle or array or other supports set forth herein previously. In further embodiments, a solution-phase primary label or solution-phase secondary label can be used for separating a proteolytic product from a protease substrate. For example, a solution phase label can be used to monitor separation of the substrate and product in a separation method such as chromatography, flow sorting, electrophoresis, extraction or others known in the art as described, for example, in Scopes, *Protein Purification* 3$^{rd}$ Ed. Springer Verlag New York (1994).

The invention further provides a method in which protease activity can be determined as a gain of signal for a plurality of protease substrates. The method can include the steps of (a) providing a plurality of protease substrates each having a protein moiety attached to a nucleic acid moiety and a ligand moiety, wherein the sequence of each nucleic acid moiety is unique to the sequence of a different protein moiety; (b) contacting the protease substrates with at least one protease under conditions wherein the at least one protease catalyzes cleavage of the protein moieties, thereby producing proteolytic products wherein the nucleic acid moieties are separated from the protein moieties and the ligand moieties; (c) contacting the proteolytic products with at least one receptor under conditions wherein the ligand moieties bind to the at least one receptor to form complexes; (d) separating the complexes from the nucleic acid moieties, thereby forming separation products comprising the nucleic acid moieties; (e) contacting the separation products with nucleic acid probes under conditions wherein the nucleic acid moieties hybridize to complementary sequences of the probes; and (f) detecting hybridization of the separation products to the probes, thereby determining activity of the at least one protease.

In embodiments wherein a plurality of proteolytic products are detected following separation from protease substrates, separation can be mediated by substantially the same ligand moiety attached to each protease substrate. Thus, a receptor, or a group of receptors having affinity for substantially the same ligand, can be used for separation of the plurality of protease products from the protease substrates from which they were derived. For example, a receptor can be used to carry out separation in a format wherein a plurality of proteolytic products is present simultaneously in the same tube. The use of the same receptor for a plurality of proteolytic products can provide for more efficient separation in such multiplex formats. However, the use of substantially the same ligand for a plurality of proteolytic products can also be used in formats where proteolytic products are individually separated from the protease substrates. Exemplary formats include, but are not limited to, individual assays or multiple assays performed sequentially.

A plurality of different proteolytic products can be separated from other reaction components based on the use of different ligands. The different ligands can have affinity for the same receptor or for different receptors. For example, biotin and any number of different biotin analogs having affinity for avidin or streptavidin can be attached to different proteolytic products and will behave as substantially the same ligand when used avidin-based or streptavidin-based separation. Alternatively the use of different ligands having affinity for different receptors can be used to subfractionate different protease substrates or proteolytic products. For example, different subpopulations of protease substrates or proteolytic products can each be attached to different ligands and the different subpopulations can be separated from each other using different receptors having specificity for the different ligands.

The methods set forth herein can be used to identify one or more inhibitors for a protease. A known or putative inhibitor can be included in a protease reaction such as those exemplified herein. The activity of the inhibitor can be determined using analysis methods known in the art including, for example, comparison to a similar protease reaction carried out in the absence of the inhibitor or enzyme kinetic methods such as those set forth above. The invention is particularly useful for determining the activity for a plurality of protease inhibitors. For example, the activity for a plurality of protease inhibitors can be determined in a multiplex assay carried out in a single tube and including at least one protease and at least one protease substrate. A multiplex reaction can include at least about 2, 3, 4, 5, 8, 10, 15, 20, 24, 30, 40, 48, 50, 60, 70, 80, 90, 96, 100, 200, 300, 386, 400, 500, 1000 or more different protease inhibitors. Furthermore, a multiplex reaction can be carried out with fewer protease inhibitors if desired including, for example, at most about a billion, million, 100,000, 10,000, 1,000, 500, 386, 96, 48, 8 or 5 different protease inhibitors. Thus, the invention can be used to screen for new protease inhibitors and to identify an inhibitor having specificity for a particular protease, group of proteases or family of proteases.

A protease assay of the invention can be used to characterize a biological system such as a cell, tissue, organism or group of organisms. For example, the protease activity for one or more proteases in a first system can be determined and, if desired, can be compared to the protease activity of a second biological system or to a reference protease activity. It will be understood that, in this regard, the protease activity for a biological system can be due to one or more proteases. Accordingly, the invention can be used to identify the protease complement present in a particular biological system. For example, a biological system can produce a particular signature of proteolytic activities toward a plurality of protease substrates that indicates the identity of the protease complement. As a further example, a method of the invention can be used to separately evaluate the protease activity of a biological system toward one or more individual protease substrates.

Exemplary biological systems that can be used in a method of the invention include, without limitation, a mammal such as a rodent, mouse, rat, rabbit, guinea pig, ungulate, horse, sheep, pig, goat, cow, cat, dog, primate, human or non-human primate; a plant such as Arabidopsis thaliana, corn (*Zea mays*), sorghum, oat (*oryza sativa*), wheat, rice, canola, or soybean; an algae such as Chlamydomonas reinhardtii; a nematode such as *Caenorhabditis elegans*; an insect such as *Drosophila melanogaster*, mosquito, fruit fly, honey bee or spider; a fish such as zebrafish (*Danio rerio*); a reptile; an amphibian such as a frog or *Xenopus laevis*; a

*dictyostelium discoideum*; a fungi such as *pneumocystis carinii, Takifugu rubripes*, yeast, *Saccharamoyces cerevisiae* or *Schizosaccharomyces pombe*; or a *plasmodium falciparum*. A method of the invention can also be used to detect protease activity for a prokaryote such as a bacterium, *Escherichia coli, staphylococci* or *mycoplasma pneumoniae*; an archae; a virus such as Hepatitis C virus or human immunodeficiency virus; or a viroid. A homogeneous culture or population of the above organisms can be evaluated using the invention as can a collection of several different organisms, for example, in a community or ecosystem.

A cell from which one or more proteases is obtained for use in the invention can be a normal cell or a cell displaying one or more symptom of a particular disease or condition. Thus, a protease sample used in a method of the invention can be obtained from a cancer cell, neoplastic cell, necrotic cell, cell experiencing an auto-immune condition, apoptotic cell or the like. Those skilled in the art will know or be able to readily determine methods for isolating one or more protease from a cell, bodily fluid or tissue using methods known in the art such as those described in Scopes, supra (1994) or Coligan et al., supra (2000). In particular embodiments of the invention, a crude cell lysate containing a collection of protease can be directly detected in a method of the invention without further isolation of the proteases. Alternatively, one or more proteases can be further isolated from other cellular components prior to protease assay. Proteases can be isolated using known methods including, for example, liquid phase extraction, precipitation, solid phase extraction, chromatography, centrifugation or the like. Such methods are described, for example, in Barrett et al., supra (2004), Scopes, supra (1994) or Coligan et al., supra (2000).

A method of the invention can further include steps of isolating a particular type of cell or tissue. Exemplary methods that can be used in a method of the invention to isolate a particular cell from other cells in a population include, but are not limited to, Fluorescent Activated Cell Sorting (FACS) as described, for example, in Shapiro, *Practical Flow Cytometry*, 3rd edition Wiley-Liss; (1995), density gradient centrifugation, or manual separation using micromanipulation methods with microscope assistance. Exemplary cell separation devices that are useful in the invention include, without limitation, a Beckman JE-6™ centrifugal elutriation system, Beckman Coulter EPICS ALTRA™ computer-controlled Flow Cytometer-cell sorter, Modular Flow Cytometer™ from Cytomation, Inc., Coulter Counter™ or Channelyzer™ system, density gradient apparatus, Cytocentrifuge, Beckman J-6™ centrifuge, EPICS V™ dual laser cell sorter, or EPICS PROFILE™ flow cytometer. A tissue or population of cells can also be removed by surgical techniques. For example, a tumor or cells from a tumor can be removed from a tissue by surgical methods, or conversely non-cancerous cells can be removed from the vicinity of a tumor.

The invention can be used for diagnosis or prognosis of a disease or condition. For example, the protease activity for a test cell or tissue that is known or suspected of being affected by a particular disease or condition can be determined using a method of the invention. If desired, protease activity can also be determined for a second cell or tissue that serves as a control and the results from the control cell or tissue compared to the results from the test cell or tissue. A control cell or tissue can be derived from a non-affected cell or tissue from the same individual as the test cell or tissue. Alternatively, the control cell or tissue can be obtained from a separate individual. The separate individual can be a non-affected individual that is related to the test individual within one, two, three or more generations. Alternatively, the separate individual can be effectively unrelated being many generations removed, or even of a different ethnicity. In some cases it may be useful to use a control individual having similar ethnicity as the test individual.

Protease activity determined in a method of the invention for a particular biological system can be correlated with one or more symptoms of a disease or condition. Those skilled in the art will know or be able to determine symptoms that are indicative of a disease or condition being evaluated. An exemplary reference describing symptoms for particular diseases or conditions is *The Merck Manual of Diagnosis and Therapy* 16th Ed., Edited by Berkow, Published by Merck and Co., Inc., Rahway N.J. (1992).

A method of the invention can also be used to evaluate the effect of a particular treatment on a biological system. For example, a biological system can be treated with a particular drug or agent suspected of having an effect on the system and protease activity measured for the treated system. The drug or agent can act, for example, as a protease inhibitor or activator, can act to increase protease expression, or can act to destabilize one or more protease, thereby reducing half life in its natural milieu. Comparison can be made to the protease activity for a control system that has not been treated or that has been treated to a different extent. Thus, protease activity as measured by a method of the invention can be used to evaluate dose response, efficacy, time period of response or the like for a biological system undergoing a particular treatment. If available, comparison can be made to a reference activity, for example, as stored in a database or other storage medium.

The following examples are intended to illustrate but not limit the present invention.

EXAMPLE I

Evaluating Protease Activity Using a Protein-DNA Conjugate as Substrate

This example demonstrates a singleplex assay in which protease activity is detected based on cleavage of a nucleic acid-protein conjugate.

Caspase-3 protease activity was carried out as follows. Caspase-3 protease was incubated with a caspase-3 substrate having the configuration shown in FIG. 2. Briefly, the caspase-3 substrate included a protein moiety (peptide) having a caspase-3 amino acid recognition sequence. The protein moiety was attached at its amino terminus to a FAM-labeled DNA moiety and at its carboxy terminus to a biotin. The enzymatic reactions were performed in 30 to 60 microliter volumes having substrate concentrations in the range of 20 nM to 150 nM. The enzyme concentrations ranged from a few ng/ml to a few mg/ml. The assay buffer was 50 mM Tris-HCL, pH 8.0, 1 mM $CaCl_2$, and 0.1% Tween-20 (v/v). The assay was carried out at 37° C. at varying times from 5 minutes to twelve hours.

Following incubation of the protease and substrate, the reaction mixture was extracted with streptavidin beads provided in molar excess for 15 minutes to remove uncleaved substrate (and cleaved protein fragments lacking the DNA moiety). Following removal of the streptavidin beads, the remaining mixture, containing FAM-labeled DNA fragments of the cleaved caspase-3 substrate, was diluted into GoldenGate™ hybridization buffer (Illumina, Inc., San Diego, Calif.) and hybridized onto a Sentrix® BeadArray Matrix for one hour at room temperature. The BeadArray matrix included nucleic acid probes that were complementary to the FAM-labeled DNA fragments. The array was imaged using the Ultra Imager™ (Ultra-Lum, Inc., Claremont, Calif.) set at 485 nm excitation and 535 nm emission to detect the presence of FAM on the probes.

A titration was carried out using protease reactions in which caspase-3 substrate was incubated with various concentrations of caspase-3 enzyme (from 1 micromolar to 0.01 nanomolar). A first control (No E, No SA) was evaluated using the protease assay conditions set forth above except that caspase-3 enzyme was absent and streptavidin extraction was omitted. The signal intensity resulting for the No E, No SA control indicates the maximum amount expected from the FAM present in a protease assay. A second control reaction (No E) was evaluated using conditions set forth above except that caspase-3 enzyme was absent. In this case the streptavidin extraction step is included. Thus, the No E control represents the minimum or background signal expected from a protease assay.

Figure 7:
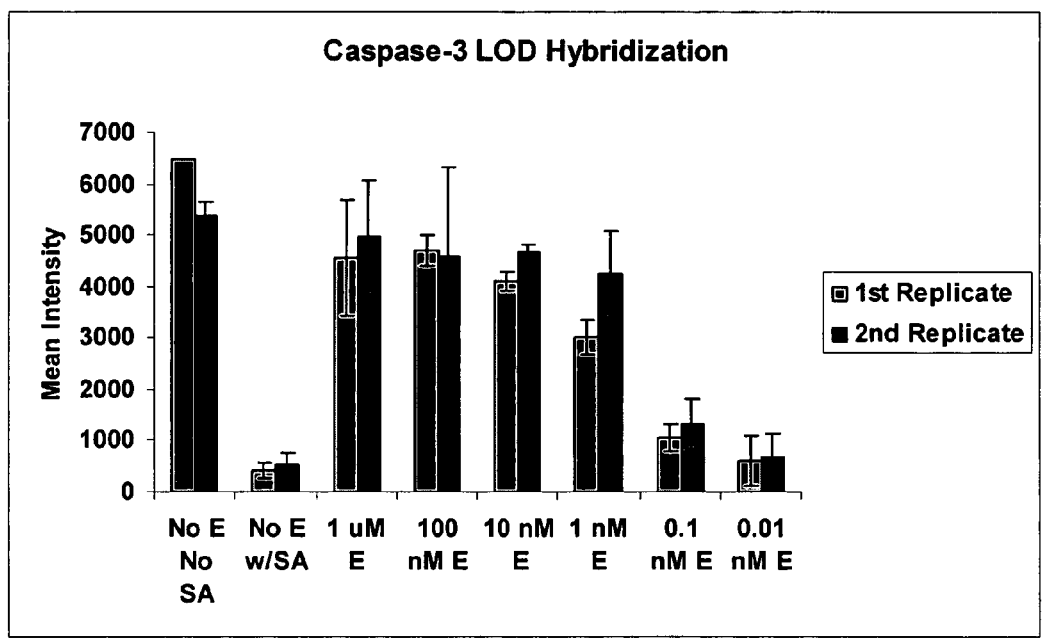
FIG. 7 shows a bar graph for the mean intensity of signal from a caspase-3 substrate detected on a BeadArray™ platform following treatment with various concentrations of enzyme approaching a limit of detection that is beyond 0.01 nM enzyme.

As shown in FIG. 7, mean intensity from probes complementary to the DNA moiety was above 5000 counts for the No E, No SA control, whereas less than 500 counts were measured for the No E control. Titration of caspase-3 enzyme indicated that nearly complete proteolysis of the caspase-3 substrate occurred in the presence of 1 micromolar, 100 nanomolar, 10 nanomolar and 1 nanomolar caspase-3 enzyme. However, as the concentration of caspase-3 enzyme was reduced to 0.1 nanomolar and 0.01 nanomolar the extent of proteolysis was also reduced.

The BeadChip arrays include multiple probes for each DNA moiety. An advantage of using multiple probes is that statistical analysis can be carried out on the detected signals to increase confidence in the results. Such statistical analysis can include standard deviation analysis (as represented by the error bars in FIG. 7). Other statistical analyses known in the art can also be used, as desired.

Figure 8:
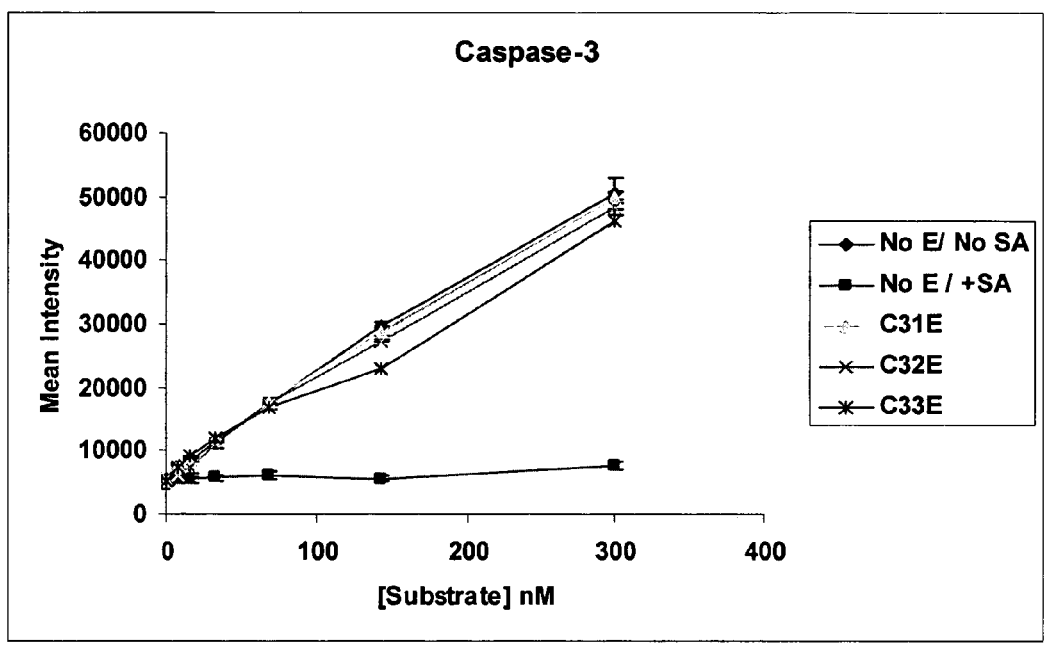
FIG. 8 shows a plot of mean intensity of signal vs. concentration for various caspase-3 substrates detected on a BeadArray™ platform following treatment in the presence or absence of caspase-3 enzyme and/or streptavidin.

Titration of caspase-3 substrate was carried out in the protease assay. As shown in FIG. 8, mean intensity for proteolyzed substrate was comparable to intensity of the No E, No SA control at each concentration tested, thereby indicating high sensitivity of the assay. C31E, C32E and C33E in the figure refers to serial dilutions of the caspase at half log intervals in the range of 300 to 17 nanomolar concentration.

Figure 9:
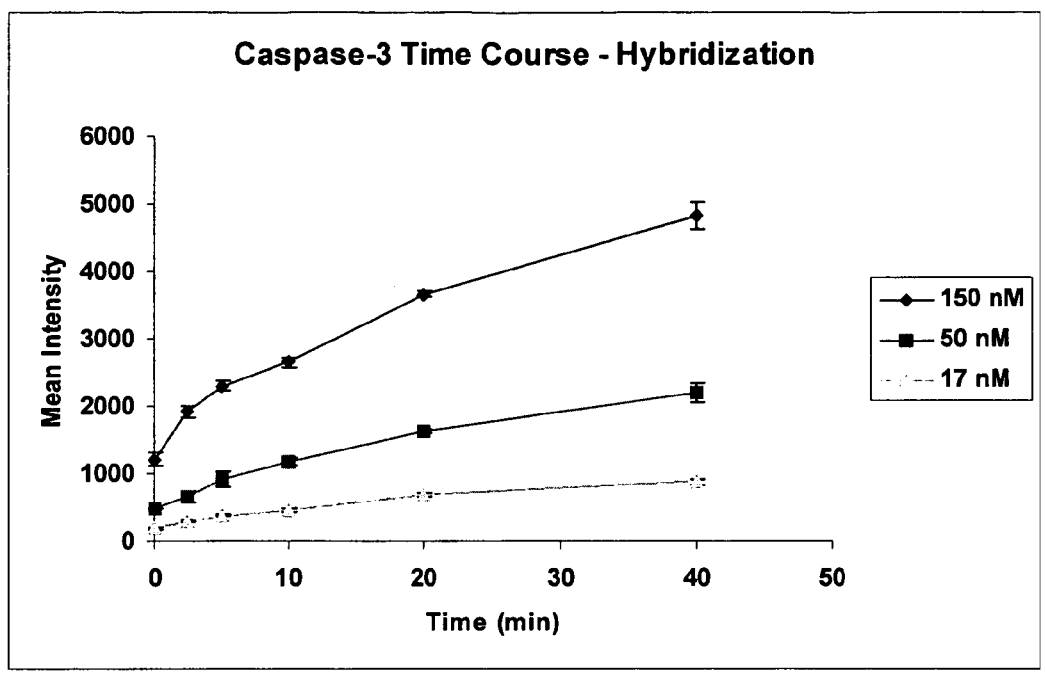
FIG. 9 shows a plot of mean intensity of signal vs. time for various concentrations of caspase-3 substrates detected on a BeadArray™ platform following treatment with caspase-3 enzyme then streptavidin-based extraction.

FIG. 9 shows a plot of mean signal intensity measured for separate assays run for various times as indicated on the x-axis. Three separate curves are presented for the three different concentrations of caspase-3 substrate that were evaluated. The results of FIG. 9 indicate that proteolysis was saturable for all three concentrations of caspase-3 substrate when reacted with caspase-3 enzyme for increasing time periods from 2 to 40 minutes.

Figure 10:
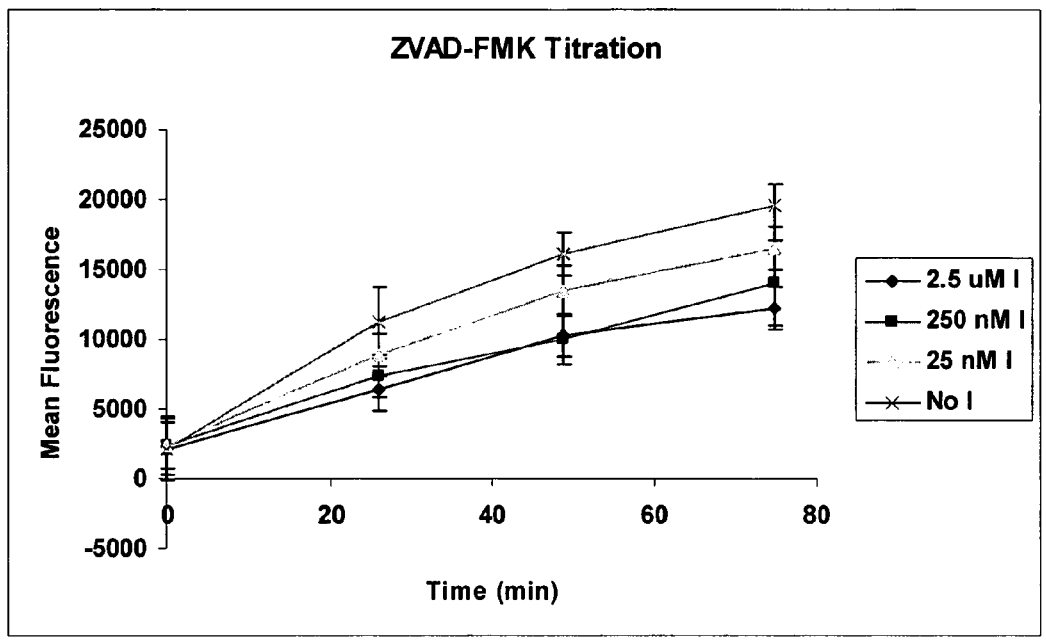
FIG. 10 shows a plot of mean intensity of signal vs. time for a caspase-3 substrate detected on a BeadArray™ platform following treatment with caspase-3 enzyme and various concentrations of caspase-3 inhibitor then streptavidin-based extraction.

An inhibition analysis was carried out in which the protease assay was performed in the presence of various concentrations of the Caspase-3 inhibitor ZVAD-FMK (EMI Biosciences, Catalog # 627610). FIG. 10 shows a plot of mean signal intensity vs. time for end point assays run in the absence of inhibitor or in the presence of various concentrations of ZVAD-FMK. Comparison of the curve obtained in the absence of inhibitor with those obtained in the presence of inhibitor indicates that as the concentration of inhibitor was increased the extent of inhibition was also increased.

These results indicate that protease activity can be evaluated to determine substrate specificity and inhibitor specificity using a method in which a protein-DNA conjugate is cleaved, unreacted nucleic acid-protein conjugate is extracted based on a first label attached to the protein moiety and, detection occurs based on a second label attached to the DNA moiety

EXAMPLE II

Multiplex Evaluation of Protease Activity on a Microarray

This example demonstrates a multiplex assay in which protease reactions for three different proteases with three different nucleic acid-protein conjugates are carried out in simultaneous reactions and in a common reaction vessel under conditions wherein each reaction can be individually evaluated.

Protease assays were carried out as set forth above in Example I except that each reaction included the three substrates 38-K, 40-MMP-2 and 41-TEV. Each substrate had a configuration similar to that shown in FIG. 2, including a protein moiety having a protease recognition sequence (for Kallikrein protease, MMP-2 protease, or Tobacco Etch Virus (TEV) protease, respectively) and a DNA moiety having a target sequence that complements a unique probe of a Sentrix® BeadArray. Three separate single-plex assays were carried out each having one of the three proteases.

Figure 11:
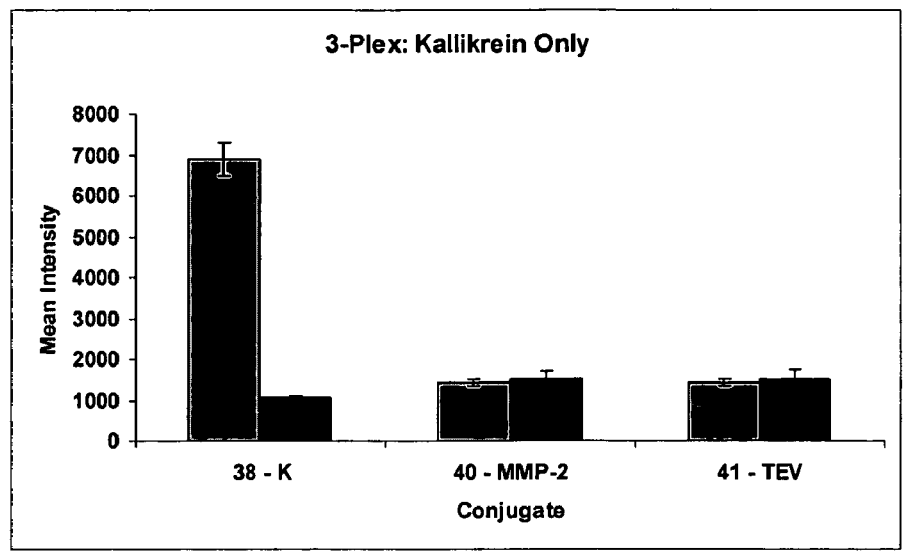
FIG. 11 shows a plot of mean intensity of signal vs. concentration for various caspase-3 substrates detected at specific probes on a BeadArray™ platform for individual reactions of each substrate with caspase-3 enzyme followed by streptavidin-based extraction.
Figure 11:
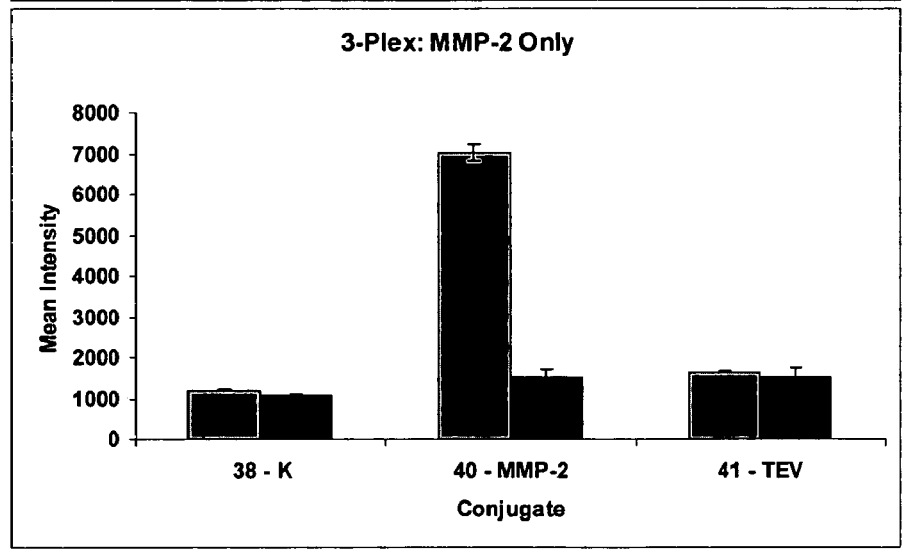
Figure 11:
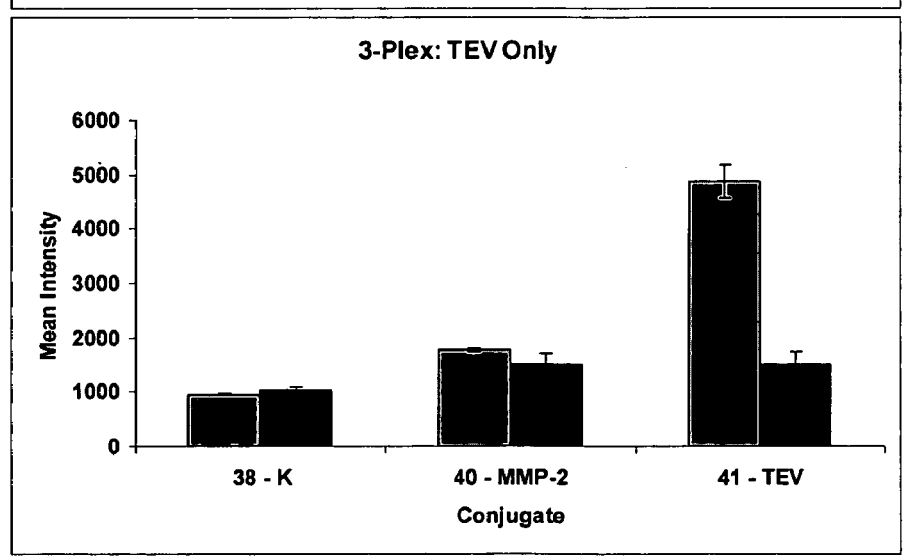

The results of the single-plex assays are shown in FIG. 11. The bar graphs show mean signal intensity detected at each set of probes that bind to the DNA moiety of a particular substrate (as listed on x-axis). Light grey bars represent signal obtained from complete reactions and dark grey bars represent signal obtained from control reactions lacking added protease. As indicated by the plots, each enzyme was specific for a single one of the three substrates under the conditions used.

Figure 12:
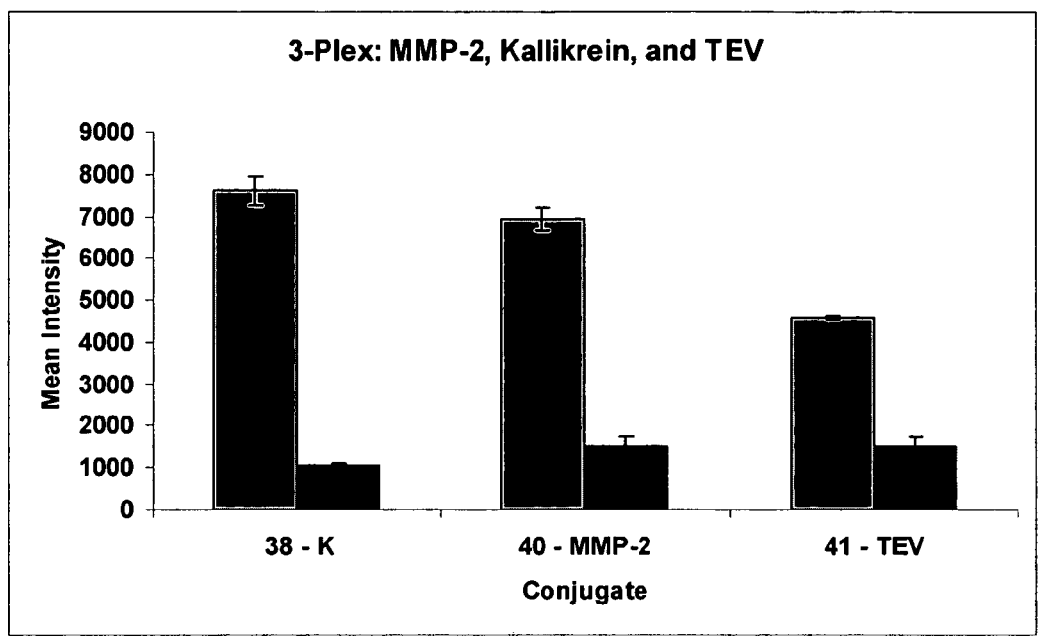
FIG. 12 shows a plot of mean intensity of signal vs. concentration for various caspase-3 substrates detected at specific probes on a BeadArray™ platform for a multiplex reaction in which all three substrates were incubated simultaneously and in the same tube with caspase-3 enzyme followed by streptavidin-based extraction.

A three-plex reaction was carried out as set forth above for the single-plex reactions except that all three proteases were present in the same reaction. The results obtained from a single array used to detect the reaction products are shown in FIG. 12. The results indicated that the three reactions could be individually evaluated based on a complex reaction mixture detected on the same array.

Throughout this application various publications, patents and patent applications have been referenced. The disclosure of these publications in their entireties is hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method of determining activity of a protease, comprising:
   (a) providing a protease substrate comprising a protein moiety attached to a nucleic acid moiety and a ligand moiety;
   (b) contacting said protease substrate with a protease under conditions wherein said protease catalyzes cleavage of said protein moiety, thereby producing a proteolytic product wherein said nucleic acid moiety is separated from at least a portion of said protein moiety and said ligand moiety;

(c) contacting said proteolytic product with a receptor under conditions wherein said ligand moiety binds to said receptor to form a complex;

(d) separating said complex from said nucleic acid moiety, wherein said receptor is attached to a solid support, thereby forming a separation product comprising said nucleic acid moiety;

(e) contacting said separation product with a probe nucleic acid under conditions wherein said nucleic acid moiety hybridizes to a complementary sequence of said probe; and (f) detecting hybridization of said separation product to said probe, thereby determining activity of said protease.

2. The method of claim 1, wherein said ligand moiety comprises a nucleic acid.

3. The method of claim 1, wherein said nucleic acid moiety is attached to a label moiety.

4. The method of claim 3, wherein said label moiety comprises a primary label.

5. The method of claim 3, wherein said label moiety comprises a secondary label.

6. The method of claim 3, wherein step (f) comprises detecting said label moiety.

7. The method of claim 1, wherein step (f) comprises adding at least one nucleotide to said probe when hybridized to said separation product and detecting said at least one nucleotide.

8. The method of claim 1, wherein step (f) comprises adding at least one nucleotide to said separation product when hybridized to said probe and detecting said at least one nucleotide.

9. A method of determining activity of at least one protease, comprising:

(a) providing a plurality of protease substrates each comprising a protein moiety attached to a nucleic acid moiety and a ligand moiety, wherein the sequence of each nucleic acid moiety is unique to the sequence of a different protein moiety;

(b) contacting said protease substrates with at least one protease under conditions wherein said at least one protease catalyzes cleavage of said protein moieties, thereby producing proteolytic products wherein said nucleic acid moieties are separated from at least a portion of said protein moieties and said ligand moieties;

(c) contacting said proteolytic products with at least one receptor under conditions wherein said ligand moieties bind to said at least one receptor to form complexes;

(d) separating said complexes from said nucleic acid moieties, wherein said at least one receptor is attached to a solid support, thereby forming separation products comprising said nucleic acid moieties;

(e) contacting said separation products with nucleic acid probes under conditions wherein said nucleic acid moieties hybridize to complementary sequences of said probes; and (f) detecting hybridization of said separation products to said probes, thereby determining activity of said at least one protease.

10. The method of claim 9, wherein said ligand moiety comprises a nucleic acid.

11. The method of claim 9, wherein each of said protease substrates comprises a ligand moiety that is substantially the same.

12. The method of claim 9, wherein said nucleic acid moieties are attached to label moieties.

13. The method of claim 12, wherein said label moieties each comprise a primary label.

14. The method of claim 12, wherein said label moieties each comprise a secondary label.

15. The method of claim 12, wherein step (f) comprises detecting said label moieties.

16. The method of claim 12, wherein each of said different protease substrates comprises a label moiety that is substantially the same.

17. The method of claim 9, wherein step (f) comprises adding at least one nucleotide to each of said probes when hybridized to said separation product and detecting said at least one nucleotide.

18. The method of claim 9, wherein step (f) comprises adding at least one nucleotide to each of said separation products when hybridized to said probes and detecting said at least one nucleotide.

19. The method of claim 9, wherein step (b) comprises contacting each of said protease substrates with a plurality of proteases under conditions wherein said proteases catalyze cleavage of said protein moieties, thereby producing proteolytic products wherein said nucleic acid moieties are separated from said protein moieties and said ligand moieties.

20. The method of claim 19, wherein said protease substrates are simultaneously contacted with said plurality of proteases in the same reaction vessel.

21. The method of claim 9, wherein step (e) comprises contacting said separation products with nucleic acid probes simultaneously and in the same reaction vessel under conditions wherein said nucleic acid moieties hybridizes to complementary sequences of said probes.

22. The method of claim 9, wherein said nucleic acid probes comprise an array of probes attached to one or more solid support.

23. The method of claim 1, wherein said protease substrate is in liquid-phase.

24. The method of claim 23, wherein step (b) comprises contacting said protease substrate with a protease under liquid phase conditions wherein said protease catalyzes cleavage of said protein moiety, thereby producing a proteolytic product wherein said nucleic acid moiety is separated from at least a portion of said protein moiety and said ligand moiety.

25. The method of claim 1, wherein said probe is attached to a solid support.

26. The method of claim 25, wherein said probe is attached at a discrete location on an array of probes.

27. The method of claim 9, wherein said plurality of protease substrates are in liquid-phase.

28. The method of claim 27, wherein step (b) comprises contacting said protease substrates with at least one protease under liquid-phase conditions wherein said at least one protease catalyzes cleavage of said protein moieties, thereby producing soluble proteolytic products wherein said nucleic acid moieties are separated from at least a portion of said protein moieties and said ligand moieties.

29. The method of claim 9, wherein said probes are attached to a solid support.

30. The method of claim 29, wherein said probes are attached at discrete locations on an array of probes.

* * * * *